US011529476B2

(12) United States Patent
Hunter et al.

(10) Patent No.: US 11,529,476 B2
(45) Date of Patent: Dec. 20, 2022

(54) DRY POWDER DELIVERY DEVICE AND METHODS OF USE

(71) Applicant: PNEUMA RESPIRATORY, INC., Boone, NC (US)

(72) Inventors: Charles Eric Hunter, Boone, NC (US); John H. Hebrank, Durham, NC (US); Louis Thomas Germinario, Kingsport, TN (US)

(73) Assignee: Pneuma Respiratory, Inc., Boone, NC (US)

( * ) Notice: Subject to any disclaimer, the term of this patent is extended or adjusted under 35 U.S.C. 154(b) by 163 days.

(21) Appl. No.: 16/615,278

(22) PCT Filed: May 21, 2018

(86) PCT No.: PCT/US2018/033704
§ 371 (c)(1),
(2) Date: Nov. 20, 2019

(87) PCT Pub. No.: WO2018/213834
PCT Pub. Date: Nov. 22, 2018

(65) Prior Publication Data

US 2021/0275760 A1 Sep. 9, 2021

Related U.S. Application Data

(60) Provisional application No. 62/508,748, filed on May 19, 2017.

(51) Int. Cl.
*A61M 15/00* (2006.01)

(52) U.S. Cl.
CPC .... *A61M 15/0091* (2013.01); *A61M 15/0048* (2014.02); *A61M 2202/064* (2013.01);
(Continued)

(58) Field of Classification Search
CPC .......... A61M 15/0091; A61M 15/0048; A61M 2202/064; A61M 2205/3306;
(Continued)

(56) References Cited

U.S. PATENT DOCUMENTS 3,934,585 A 1/1976 Maurice
3,970,250 A 7/1976 Drews
(Continued)

FOREIGN PATENT DOCUMENTS

AU 2012258488 1/2013
CA 2364248 8/2006
(Continued)

OTHER PUBLICATIONS

Steller, "Microcontroller Based Diagnostic Smart Inhaler," University of Cincinnati, Dec. 7, 2014, 63 pages.
(Continued)

*Primary Examiner* — Victoria Murphy
(74) *Attorney, Agent, or Firm* — Polsinelli PC

(57) ABSTRACT

A dry powder aerosol delivery device and related methods for delivering precise and repeatable dosages to a subject for pulmonary use is disclosed. The dry powder aerosol delivery device includes a housing, a cartridge, and a dry powder dispersion mechanism, and at least one differential pressure sensor. The dry powder delivery device is automatically breath actuated by the user when the differential pressure sensor senses a predetermined pressure change within housing. The dry powder aerosol delivery device is then actuated to generate a plume of particles having an average ejected particle diameter within the respirable size range, e.g., less than about 5-6 μm, so as to target the pulmonary system of the user.

9 Claims, 11 Drawing Sheets

(52) U.S. Cl.
CPC .............. *A61M 2205/3306* (2013.01); *A61M 2205/3331* (2013.01); *A61M 2205/3576* (2013.01); *A61M 2205/8225* (2013.01); *A61M 2206/11* (2013.01)

(58) Field of Classification Search
CPC .. A61M 2205/3331; A61M 2205/3576; A61M 2205/8225; A61M 2206/11; A61M 11/02; A61M 11/003; A61M 16/0833; A61M 16/125; A61M 16/14; A61M 2016/0021; A61M 2016/0027; A61M 2202/0225; A61M 2205/3569; A61M 2205/3592; A61M 2205/505
See application file for complete search history.

(56) References Cited

U.S. PATENT DOCUMENTS

| | | | |
|---|---|---|---|
| 5,021,701 A | 6/1991 | Takahashi et al. | |
| 5,164,740 A | 11/1992 | Ivri | |
| 5,363,842 A | 11/1994 | Mishelevich et al. | |
| 5,487,378 A | 1/1996 | Robertson et al. | |
| 5,586,550 A | 12/1996 | Ivri et al. | |
| 5,607,410 A | 3/1997 | Branch | |
| 5,630,793 A | 5/1997 | Rowe | |
| 5,758,637 A | 6/1998 | Ivri et al. | |
| 5,826,570 A | 10/1998 | Goodman et al. | |
| 5,828,394 A | 10/1998 | Khuri-Yakub et al. | |
| 5,881,716 A | 3/1999 | Wirch et al. | |
| 5,884,620 A | 3/1999 | Gonda et al. | |
| 5,894,841 A | 4/1999 | Voges | |
| 5,906,202 A | 5/1999 | Schuster et al. | |
| 5,938,117 A | 8/1999 | Ivri | |
| 5,979,247 A | 11/1999 | Kizawa | |
| 6,011,062 A | 1/2000 | Schneider et al. | |
| 6,062,212 A | 5/2000 | Davison et al. | |
| 6,071,498 A | 6/2000 | Narodylo et al. | |
| 6,085,740 A | 7/2000 | Ivri et al. | |
| 6,158,431 A | 12/2000 | Poole | |
| 6,196,219 B1 | 3/2001 | Hess et al. | |
| 6,235,177 B1 | 5/2001 | Borland et al. | |
| 6,358,058 B1 | 3/2002 | Strupat et al. | |
| 6,443,146 B1 * | 9/2002 | Voges ............... | A61M 15/0023 128/200.14 |
| 6,511,718 B1 | 1/2003 | Paz de Araujo et al. | |
| 6,615,826 B1 | 9/2003 | Gabrio et al. | |
| 6,629,524 B1 | 10/2003 | Goodall et al. | |
| 6,637,430 B1 | 10/2003 | Voges et al. | |
| 6,896,910 B2 | 5/2005 | Kim et al. | |
| 6,978,941 B2 | 12/2005 | Litherland et al. | |
| 6,981,499 B2 | 1/2006 | Anderson et al. | |
| 7,191,777 B2 | 3/2007 | Brand et al. | |
| 7,198,044 B2 | 4/2007 | Trueba | |
| 7,219,664 B2 | 5/2007 | Ruckdeschel et al. | |
| 7,628,339 B2 | 12/2009 | Ivri et al. | |
| 7,648,957 B2 | 1/2010 | Heyden et al. | |
| 7,708,011 B2 | 5/2010 | Hochrainer et al. | |
| 7,883,031 B2 | 2/2011 | Collins, Jr. et al. | |
| 7,900,625 B2 | 3/2011 | Kleinstreuer et al. | |
| 7,954,486 B2 | 6/2011 | Papania et al. | |
| 7,976,140 B2 | 7/2011 | Umeda | |
| 8,012,136 B2 | 9/2011 | Collins, Jr. et al. | |
| 8,367,734 B1 | 2/2013 | Gao et al. | |
| 8,474,452 B2 | 7/2013 | Gumaste et al. | |
| 8,545,463 B2 | 10/2013 | Collins, Jr. et al. | |
| 8,555,874 B2 | 10/2013 | Fink et al. | |
| 8,616,195 B2 | 12/2013 | Power et al. | |
| 8,684,980 B2 | 4/2014 | Hunter et al. | |
| 8,733,935 B2 | 5/2014 | Ballou, Jr. et al. | |
| 8,753,308 B2 | 6/2014 | Palmer et al. | |
| 8,936,021 B2 | 1/2015 | Collins, Jr. | |
| 8,985,100 B2 | 3/2015 | Minocchieri et al. | |
| 9,022,027 B2 | 5/2015 | Addington et al. | |
| 9,087,145 B2 | 7/2015 | Ballou, Jr. et al. | |
| 9,227,029 B2 | 1/2016 | Addington et al. | |
| 9,242,054 B2 | 1/2016 | Fink et al. | |
| 9,452,274 B2 | 9/2016 | Addington et al. | |
| 9,463,486 B2 | 10/2016 | Wilkerson et al. | |
| 9,539,604 B2 | 1/2017 | Wilkerson et al. | |
| 9,956,360 B2 | 5/2018 | Germinario et al. | |
| 9,962,507 B2 | 5/2018 | Germinario et al. | |
| 10,449,314 B2 | 10/2019 | Germinario et al. | |
| 10,525,220 B2 | 1/2020 | Hunter et al. | |
| 10,568,543 B2 | 2/2020 | Yan | |
| 10,857,310 B2 | 12/2020 | Muellinger et al. | |
| 10,898,666 B2 | 1/2021 | Germinario et al. | |
| 2002/0002975 A1 | 1/2002 | Power | |
| 2002/0032387 A1 | 3/2002 | Geva et al. | |
| 2002/0046750 A1 | 4/2002 | Gonda et al. | |
| 2002/0071871 A1 | 6/2002 | Snyder et al. | |
| 2002/0077369 A1 | 6/2002 | Noolandi et al. | |
| 2002/0121274 A1 | 9/2002 | Borland et al. | |
| 2003/0062042 A1 | 4/2003 | Wensley et al. | |
| 2003/0072717 A1 | 4/2003 | Reinhold et al. | |
| 2003/0098022 A1 | 5/2003 | Nakao et al. | |
| 2003/0101991 A1 | 6/2003 | Trueba | |
| 2003/0127538 A1 | 7/2003 | Patel et al. | |
| 2003/0140921 A1 | 7/2003 | Smith et al. | |
| 2003/0150445 A1 | 8/2003 | Power et al. | |
| 2003/0196654 A1 | 10/2003 | Stein | |
| 2003/0205229 A1 | 11/2003 | Crockford et al. | |
| 2004/0009231 A1 | 1/2004 | Jackson et al. | |
| 2004/0084044 A1 | 5/2004 | Childers et al. | |
| 2004/0139963 A1 | 7/2004 | Ivri et al. | |
| 2004/0195403 A1 | 10/2004 | Atterybury et al. | |
| 2004/0215157 A1 | 10/2004 | Peclat et al. | |
| 2004/0256487 A1 | 12/2004 | Collins, Jr. et al. | |
| 2005/0011514 A1 | 1/2005 | Power et al. | |
| 2005/0077315 A1 | 4/2005 | Pavlu et al. | |
| 2005/0121025 A1 * | 6/2005 | Gamard .............. | A61M 15/009 128/200.23 |
| 2005/0150489 A1 | 7/2005 | Dunfield et al. | |
| 2005/0172476 A1 | 8/2005 | Stone et al. | |
| 2005/0172958 A1 | 8/2005 | Singer et al. | |
| 2005/0217666 A1 | 10/2005 | Fink et al. | |
| 2005/0224075 A1 | 10/2005 | Childers et al. | |
| 2005/0236501 A1 | 10/2005 | Zimlich, Jr. et al. | |
| 2007/0023036 A1 | 2/2007 | Grychowski et al. | |
| 2007/0044793 A1 | 3/2007 | Kleinstreuer et al. | |
| 2007/0083677 A1 | 4/2007 | Cecka et al. | |
| 2007/0119969 A1 | 5/2007 | Collins, Jr. et al. | |
| 2007/0125370 A1 | 6/2007 | Denyer et al. | |
| 2007/0157931 A1 | 7/2007 | Parker et al. | |
| 2007/0240714 A1 | 10/2007 | Dunne et al. | |
| 2007/0248645 A1 | 10/2007 | Bague et al. | |
| 2007/0267010 A1 | 11/2007 | Fink et al. | |
| 2008/0000470 A1 | 1/2008 | Minocchieri et al. | |
| 2008/0059228 A1 | 3/2008 | Bossi et al. | |
| 2008/0142010 A1 | 6/2008 | Weaver et al. | |
| 2008/0243050 A1 | 10/2008 | Power et al. | |
| 2008/0271732 A1 | 11/2008 | Weaver et al. | |
| 2008/0283057 A1 | 11/2008 | Rohrschneider et al. | |
| 2008/0295827 A1 | 12/2008 | Kobayashi | |
| 2008/0308096 A1 | 12/2008 | Borgschulte et al. | |
| 2009/0038610 A1 | 2/2009 | Bogh et al. | |
| 2009/0093772 A1 | 4/2009 | Genosar et al. | |
| 2009/0107492 A1 | 4/2009 | Ooida | |
| 2009/0114218 A1 | 5/2009 | Veatch | |
| 2009/0114742 A1 | 5/2009 | Collins, Jr. | |
| 2009/0118243 A1 | 5/2009 | Gjorstrup | |
| 2009/0134235 A1 | 5/2009 | Ivri | |
| 2009/0167812 A1 | 7/2009 | Asai et al. | |
| 2009/0192443 A1 | 7/2009 | Collins, Jr. | |
| 2009/0212133 A1 | 8/2009 | Collins, Jr. | |
| 2009/0235925 A1 | 9/2009 | Power et al. | |
| 2009/0270752 A1 | 10/2009 | Coifman | |
| 2009/0272818 A1 | 11/2009 | Valpey, III et al. | |
| 2009/0314292 A1 | 12/2009 | Overfield et al. | |
| 2009/0317496 A1 | 12/2009 | Park et al. | |
| 2010/0037894 A1 | 2/2010 | Rouse et al. | |
| 2010/0078013 A1 | 4/2010 | Power et al. | |
| 2010/0089395 A1 | 4/2010 | Power et al. | |
| 2010/0156995 A1 | 6/2010 | Kanda et al. | |
| 2010/0181387 A1 | 7/2010 | Zaffaroni et al. | |

(56) References Cited

U.S. PATENT DOCUMENTS

| | | |
|---|---|---|
| 2010/0222752 A1 | 9/2010 | Collins, Jr. et al. |
| 2010/0282247 A1 | 11/2010 | Kadrichu et al. |
| 2011/0108025 A1 | 5/2011 | Fink et al. |
| 2011/0114090 A1 | 5/2011 | Piper |
| 2011/0230820 A1 | 9/2011 | Lillis et al. |
| 2011/0253139 A1 | 10/2011 | Guthrie et al. |
| 2011/0253805 A1 | 10/2011 | Lee |
| 2012/0037154 A1 | 2/2012 | Gallem et al. |
| 2012/0048265 A1 | 3/2012 | Smaldone |
| 2012/0266878 A1 | 10/2012 | Watanabe et al. |
| 2012/0291781 A1 | 11/2012 | Kaufmann et al. |
| 2013/0079732 A1 | 3/2013 | Burt et al. |
| 2013/0150812 A1 | 6/2013 | Hunter et al. |
| 2013/0172830 A1 | 7/2013 | Hunter et al. |
| 2013/0239956 A1 | 9/2013 | Schulz et al. |
| 2013/0267864 A1 | 10/2013 | Addington et al. |
| 2013/0269694 A1 | 10/2013 | Patton et al. |
| 2013/0284165 A1 | 10/2013 | Krimsky |
| 2013/0299607 A1 | 11/2013 | Wilkerson et al. |
| 2013/0327323 A1 | 12/2013 | Rubin |
| 2013/0330400 A1 | 12/2013 | Perkins et al. |
| 2013/0334335 A1 | 12/2013 | Wilkerson et al. |
| 2013/0334339 A1 | 12/2013 | Xu |
| 2014/0037735 A1 | 2/2014 | Montgomery |
| 2014/0116426 A1 | 5/2014 | Mullinger et al. |
| 2014/0187969 A1 | 7/2014 | Hunter et al. |
| 2014/0190496 A1 | 7/2014 | Wensley et al. |
| 2014/0213925 A1 | 7/2014 | Chan et al. |
| 2014/0283859 A1 | 9/2014 | Minskoff et al. |
| 2014/0336618 A1 | 11/2014 | Wilkerson et al. |
| 2015/0018694 A1 | 1/2015 | Gomo |
| 2015/0101596 A1 | 4/2015 | Hogan |
| 2015/0136129 A1 | 5/2015 | Mehadevan et al. |
| 2015/0136155 A1 | 5/2015 | Verleur et al. |
| 2015/0164375 A1 | 6/2015 | Schindhelm et al. |
| 2015/0174348 A1 | 6/2015 | Tunnell et al. |
| 2015/0196060 A1 | 7/2015 | Wensley et al. |
| 2015/0273165 A1 | 10/2015 | Hadash |
| 2015/0283339 A1 | 10/2015 | Mahadevan et al. |
| 2015/0328151 A1 | 11/2015 | Ballou, Jr. et al. |
| 2015/0352301 A1 | 12/2015 | Stedman et al. |
| 2016/0001018 A1 | 1/2016 | Fink et al. |
| 2016/0001019 A1 | 1/2016 | Fink et al. |
| 2016/0082208 A1 | 3/2016 | Ballam et al. |
| 2016/0106341 A1 | 4/2016 | Adam et al. |
| 2016/0129182 A1 | 5/2016 | Schuster et al. |
| 2016/0166768 A1 | 6/2016 | Edwards et al. |
| 2016/0213864 A1 | 7/2016 | Eilat et al. |
| 2016/0213866 A1 | 7/2016 | Tan |
| 2016/0245830 A1 | 8/2016 | Mace et al. |
| 2016/0310982 A1 | 10/2016 | Von Hollen |
| 2016/0325055 A1 | 11/2016 | Cameron |
| 2016/0354557 A1 | 12/2016 | McPherson Allnutt et al. |
| 2017/0035924 A1 | 2/2017 | Yang et al. |
| 2017/0039344 A1 | 2/2017 | Bitran et al. |
| 2017/0106153 A1* | 4/2017 | Davidson .......... A61M 15/0028 |
| 2017/0106155 A1 | 4/2017 | Reed et al. |
| 2017/0128677 A1 | 5/2017 | Eilat et al. |
| 2017/0158776 A1 | 6/2017 | Feltquate et al. |
| 2017/0203058 A1* | 7/2017 | Davidson .............. A61K 31/05 |
| 2017/0203323 A1 | 7/2017 | Gschwind et al. |
| 2017/0224706 A1 | 8/2017 | Surber |
| 2017/0270260 A1 | 9/2017 | Shetty et al. |
| 2017/0274163 A1 | 9/2017 | Oliveras et al. |
| 2017/0304565 A1 | 10/2017 | Allosery |
| 2017/0304566 A1 | 10/2017 | Allosery |
| 2017/0319796 A1 | 11/2017 | Germinario et al. |
| 2017/0319797 A1 | 11/2017 | Germinario et al. |
| 2017/0333646 A1* | 11/2017 | Hemy ................ A61M 15/0028 |
| 2018/0021530 A1 | 1/2018 | Fink et al. |
| 2018/0056018 A1 | 3/2018 | Canvin et al. |
| 2018/0116871 A1 | 5/2018 | Hunter et al. |
| 2018/0193175 A1 | 7/2018 | Bluecher et al. |
| 2018/0317557 A1 | 11/2018 | Monsees et al. |
| 2018/0344955 A1 | 12/2018 | Germinario et al. |
| 2018/0369515 A1 | 12/2018 | Germinario et al. |
| 2019/0117907 A1 | 4/2019 | Germinario et al. |
| 2019/0125985 A1 | 5/2019 | Germinario et al. |
| 2019/0125986 A1 | 5/2019 | Germinario et al. |
| 2019/0125987 A1 | 5/2019 | Germinario et al. |
| 2019/0134330 A1 | 5/2019 | Germinario et al. |
| 2019/0224426 A1 | 7/2019 | Farina et al. |
| 2019/0358420 A1 | 11/2019 | Hunter et al. |
| 2020/0147325 A1 | 5/2020 | Wilson et al. |
| 2020/0230329 A1 | 7/2020 | Danek |
| 2020/0276398 A1 | 9/2020 | Hebrank et al. |
| 2020/0289770 A1 | 9/2020 | Hebrank et al. |
| 2020/0345588 A1 | 11/2020 | Merrell et al. |
| 2020/0353186 A1 | 11/2020 | Hebrank et al. |
| 2021/0106772 A1 | 4/2021 | Hebrank et al. |
| 2021/0236745 A1 | 8/2021 | Germinario et al. |
| 2022/0001122 A1 | 1/2022 | Hunter et al. |
| 2022/0296823 A1 | 9/2022 | Hebrank et al. |

FOREIGN PATENT DOCUMENTS

| | | | |
|---|---|---|---|
| CH | 715947 | 11/2020 | |
| CN | 1788806 | 6/2006 | |
| CN | 104511072 | 4/2015 | |
| CN | 204995458 | 1/2016 | |
| CN | 205019058 | 2/2016 | |
| EP | 2724741 | 4/2014 | |
| JP | H11-042219 | 2/1999 | |
| JP | 2003-265994 | 9/2003 | |
| JP | 2006-68508 | 3/2006 | |
| KR | 10-2019-122453 | 10/2019 | |
| WO | WO 93/12823 | 7/1993 | |
| WO | WO 96/09846 | 4/1996 | |
| WO | WO 96/14163 | 5/1996 | |
| WO | WO 98/48873 | 11/1998 | |
| WO | WO 00/10634 | 3/2000 | |
| WO | WO 00/47335 | 8/2000 | |
| WO | WO 01/85244 | 11/2001 | |
| WO | WO 01/87378 | 11/2001 | |
| WO | 03/020349 A2 | 3/2003 | |
| WO | WO 03/059413 | 7/2003 | |
| WO | WO 2004/078025 | 9/2004 | |
| WO | WO 2006/013952 | 2/2006 | |
| WO | WO 2006/083014 | 8/2006 | |
| WO | WO-2006108558 A1 * | 10/2006 | ............ A61M 11/06 |
| WO | WO 2007/107160 | 9/2007 | |
| WO | WO 2008/056986 | 5/2008 | |
| WO | WO 2008/058941 | 5/2008 | |
| WO | WO 2008/116165 | 9/2008 | |
| WO | WO 2009/012371 | 1/2009 | |
| WO | WO 2009/111612 | 9/2009 | |
| WO | WO 2010/065452 | 6/2010 | |
| WO | WO 2011/083377 | 7/2011 | |
| WO | WO 2011/091268 | 7/2011 | |
| WO | WO 2011/163272 | 12/2011 | |
| WO | WO 2012/026963 | 3/2012 | |
| WO | WO 2013/098334 | 7/2013 | |
| WO | WO 2013/158352 | 10/2013 | |
| WO | WO 2013/158967 | 10/2013 | |
| WO | WO 2013/173321 | 11/2013 | |
| WO | WO 2015/136529 | 9/2015 | |
| WO | WO 2016/001924 | 1/2016 | |
| WO | WO 2016/003738 | 1/2016 | |
| WO | WO 2017/015303 | 1/2017 | |
| WO | WO 2017/056103 | 4/2017 | |
| WO | WO 2019/071008 | 4/2019 | |
| WO | WO 2019/079461 | 4/2019 | |
| WO | WO 2019/219865 | 11/2019 | |
| WO | WO 2020/072478 | 4/2020 | |
| WO | WO 2020/141424 | 7/2020 | |
| WO | WO 2020/154497 | 7/2020 | |
| WO | WO 2020/227717 | 11/2020 | |
| WO | WO 2020/264501 | 12/2020 | |

OTHER PUBLICATIONS

Carvalho et al., "The function and performance of aqueous aerosol devices for inhalation therapy," Journal of Pharmacy and Pharmacology, vol. 68, No. 5, Apr. 8, 2016, pp. 556-578.

(56) References Cited

OTHER PUBLICATIONS

Copley, "Understanding cascade impaction and its importance for inhaler testing," Copley Scientific, Copley White Paper [serial online], Jul. 2007 [retrieved on May 7, 2017]. Retrieved from the Internet: URL: http://www.copleyscientific.com/files/ww/articles/Understanding%20Cascade%20Impaction%20White%20Paper.pdf; 6 pp.

Kharitonov, "Exhaled markers of inflammatory lung diseases: ready for routine monitoring?" *Swiss Med Wkly*, 2004; 134: 175-192.

Broeders et al., "Inhalation Profiles in Asthmatics and COPD Patients: Reproducibility and Effect of Instruction," *Journal of Aerosol Medicine*, vol. 16, No. 2, 2003, 131-141.

Taube et al., "Use of a portable device to record maximum inspiratory flow in relation to dyspnoea in patients with COPD," *Respiratory Medicine*, 2011, 105, 316-312.

\* cited by examiner

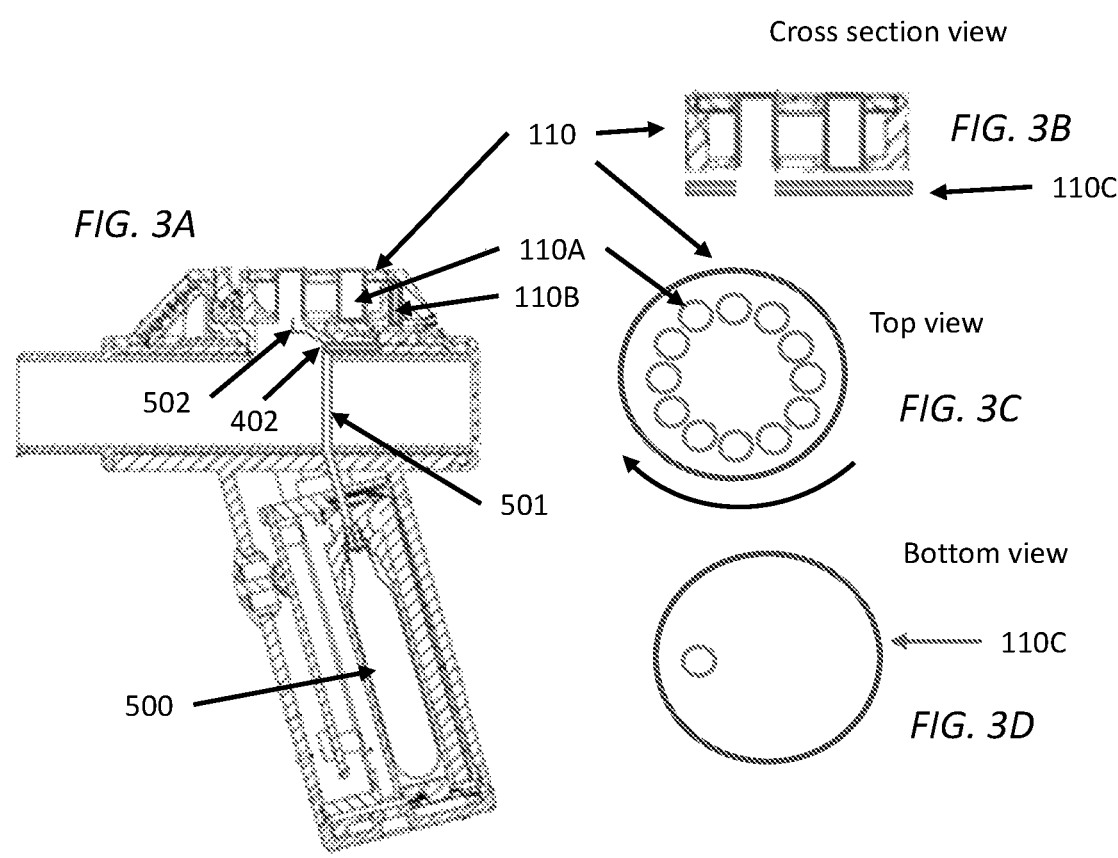

DRY POWDER DELIVERY DEVICE AND METHODS OF USE

RELATED APPLICATIONS

The present application claims benefit under 35 U.S.C. § 119 of U.S. Provisional Patent Application No. 62/508,748, filed May 19, 2017, entitled "DRY POWDER DELIVERY DEVICE AND METHODS OF USE", the contents of which are herein incorporated by reference in its entirety.

FIELD OF THE INVENTION

This disclosure relates to dry powder delivery devices and more specifically to dry powder delivery devices for the delivery of therapeutic dry powders to the pulmonary system.

BACKGROUND OF THE INVENTION

The use of inhalation devices for the treatment of a variety of respiratory diseases is an area of large interest. Inhalation provides for the delivery of therapeutic drugs to treat, e.g., asthma, COPD and site-specific conditions, with reduced systemic adverse effects. A major challenge is providing a device that delivers an accurate, consistent, and verifiable dose, with an inhalation plume size that is suitable for successful delivery of medication to the targeted location in the body such as the lung passageways.

Currently most inhaler systems such as metered dose inhalers (MDI) and pressurized metered dose inhalers (p-MDI) or pneumatic and ultrasonic-driven devices generally produce drops with high velocities and a wide range of droplet sizes including large droplet that have high momentum and kinetic energy. Droplets and aerosols with such high momentum do not reach the distal lung or lower pulmonary passageways but are deposited in the mouth and throat. As a result, larger total drug doses are required to achieve the desired deposition in targeted areas. These large doses increase the probability of unwanted side effects.

Dry powder inhalers (DPIs) are portable devices available as an alternative to MDI devices. Dry powder inhalers rely on adequate patient effort to deliver the dose. In general, the efficacy of DPIs can be affected by environmental conditions such as temperature and humidity. Since higher patient inspiratory flow is necessary to operate a DPI, they are not recommended for children less than five years of age. Unlike the MDI, where the design is relatively uniform for each device, DPI devices tend to vary depending on the device, which may contribute to patient and health care provider confusion. As such, improvements are needed to provide DPIs that provide the efficient delivery to the pulmonary system of users.

In particular, there is a need for a DPI device that delivers particles of a suitable size range, avoids aggregate formation and insures adequate particle dispersion that delivers a dose that is accurate, consistent and verifiable, and provides feedback regarding correct and consistent usage of the inhaler to patient and professional such as physician, pharmacist or therapist.

SUMMARY OF THE INVENTION

In certain aspects, the disclosure provides a breath actuated dry powder delivery device for delivering a powder as a plume of particles to the pulmonary system of a subject. In certain aspects, the disclosure relates to a dry powder delivery device and method for generating a plume of powder particles having an average diameter of less than about 5-6 µm or a range of particle size that is consistent with the particle size distribution of the original powder formulation. In certain aspects, the dry powder delivery device comprises a dry powder dispersal mechanism comprised of an energy source configured to generate a plume of powder particles having an average particle diameter of less than about 5-6 µm, or a range of particle size that is consistent with the particle size distribution of the original powder formulation.

In certain embodiments, the breath actuated dry powder delivery device may include a housing comprising a mouthpiece located at an airflow exit side of the housing, and a laminar flow element; a cartridge disposed within or removably attached to the housing, for receiving a volume of powder; a powder dispersion mechanism, the powder dispersion comprising an energy source configured to generate and disperse a plume of particles from a powder received in the cartridge; and at least one differential pressure sensor positioned within the housing.

In certain embodiments, the at least one differential pressure sensor may be configured to activate the energy source of the powder dispersion mechanism upon sensing a predetermined pressure change within the housing to thereby generate the plume of particles. The laminar flow element may be located at an airflow entrance side of the housing, wherein the housing, laminar flow element, and mouthpiece are configured to facilitate laminar airflow across an exit side of the powder dispersion mechanism and to provide sufficient laminar airflow through the housing during use. The powder dispersion mechanism may be configured to generate the plume of particles wherein at least about 70% of the particles have an average particle diameter of less than about 6 microns, such that at least about 70% of the mass of the generated particles is delivered in a respirable range to the pulmonary system of a subject during use.

Other aspects relate to methods for generating and delivering a powder as a plume of particles to the pulmonary system of a subject in a respirable range, the method comprising: (a) generating a plume of particles via an breath actuated dry powder delivery device of the disclosure, wherein at least about 70% of the particles have an average particle diameter of less than about 6 microns; and delivering the plume of particles to the pulmonary system of the subject such that at least about 70% of the mass of the generated particles is delivered in a respirable range to the pulmonary system of the subject during use.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the detailed descriptions are to be regarded as illustrative in nature and not restrictive.

BRIEF DESCRIPTION OF THE DRAWINGS

FIG. 1B and FIG. 1C illustrate exemplary locations of pressure sensors and restrictions. FIG. 1B illustrates an example where the restriction is internal to the mouthpiece tube. FIG. 1C illustrates an example where the restriction is located at the laminar flow element and the pressure is sensed as the differential between the interior of the mouthpiece tube and the pressure outside the tube. FIG. 1D illustrates a screen capture of the delta P sensor response to an inhaled breath of a 1 second duration.

FIG. 3A is a cross section view of a dry powder delivery device including a rotatable cartridge/reservoir, in accordance with an embodiment of the disclosure.

FIG. 3B is a cross section view of the rotatable cartridge/reservoir and cover disk, in accordance with an embodiment of the disclosure.

FIG. 3C is a top view of the rotatable cartridge/reservoir and cover disk, in accordance with an embodiment of the disclosure.

FIG. 3D is a bottom view of the rotatable cartridge/reservoir and cover disk, in accordance with an embodiment of the disclosure.

DETAILED DESCRIPTION

Figure 1A:
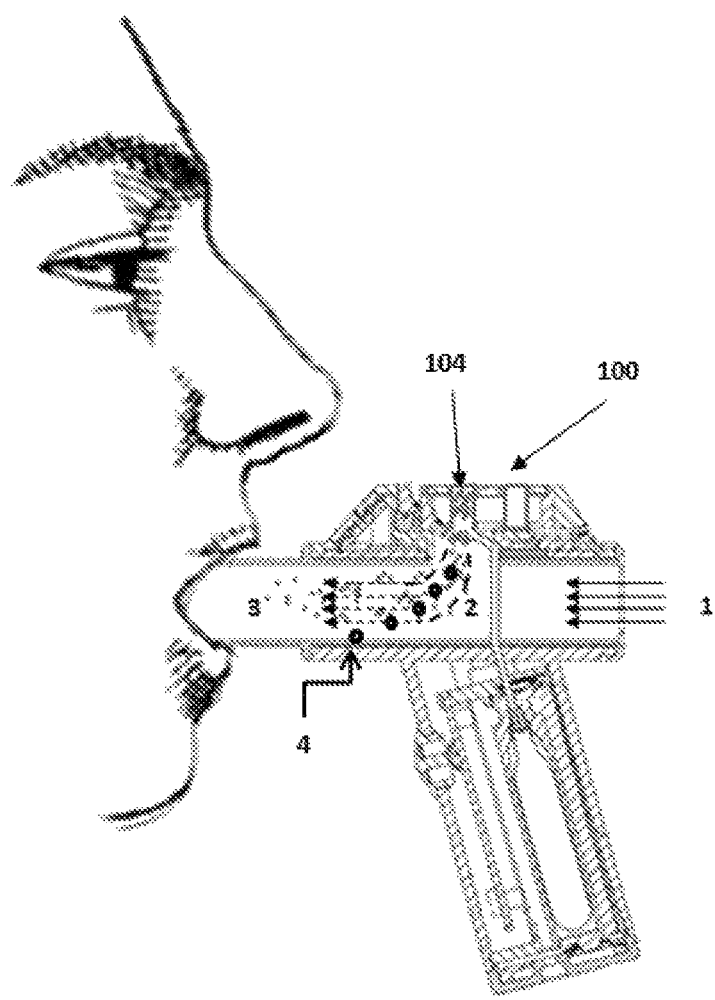
FIG. 1A illustrates a breath actuated dry powder delivery device and inertial filtering using such a device, in accordance with embodiments of the disclosure.

Effective delivery of medication to the deep pulmonary regions of the lungs through the alveoli has always posed a problem, especially to children and elderly, as well as to those with the diseased state, owing to their limited lung capacity and constriction of the breathing passageways. The impact of constricted lung passageways limits deep inspiration and synchronization of the administered dose with the inspiration/expiration cycle. For optimum deposition in alveolar airways, particles with aerodynamic diameters in the ranges of 1 to 6, more particularly 1 to 5 µm are optimal, with particles below about 4 µm shown to reach the alveolar region of the lungs, while larger particles are deposited on the tongue or strike the throat and coat the bronchial passages. Smaller particles, for example less than about 1 µm that penetrate more deeply into the lungs have a tendency to be exhaled.

In accordance with certain aspects of the disclosure, effective deposition into the lungs generally requires particles having an average particle diameter of less than about 5-6 µm. Without intending to be limited by theory, to deliver a dry powder to the lungs, a dry powder delivery device must impart a sufficiently high amount of shear force and momentum to the powder to permit dispersal of the powder, but also impart a momentum that is sufficiently low to prevent deposition on the tongue or in the back of the throat during use. In this regard, dry powder plume particles having an average particle diameter of less than about 5-6 µm are transported almost completely by motion of the plume and entrained air that carry them, and not by their own momentum.

In certain aspects, the present disclosure relates to a dry powder delivery device for delivery a medicament as a generated plume of particles to the pulmonary system of a subject and related methods of delivering safe, suitable, and repeatable dosages to the pulmonary system of a subject. In other aspects, the present disclosure also relates to a dry powder delivery device and method capable of delivering a dry powder such that an adequate and repeatable high percentage of the powder is delivered into the desired location within the airways, e.g., the alveolar airways of the subject during use. In certain embodiments, the disclosure relates to a breath actuated dry powder delivery device for delivering a powder as a plume of particles to the pulmonary system of a subject.

In certain aspects, the disclosure relates to a dry powder delivery device and method for generating a plume of dry powder particles having an average diameter of less than about 5-6 µm or a range of particle size that is consistent with the particle size distribution of the original powder formulation. In certain aspects, the dry powder delivery device comprises a dry powder dispersal mechanism comprised of an energy source configured to generate a plume of dry powder particles having an average particle diameter of less than about 5-6 µm, or a range of particle size that is consistent with the particle size distribution of the original powder formulation.

In certain embodiments, the present disclosure provides a dry powder delivery device for delivery of a dry powder to the pulmonary system of a subject, the device comprising a housing, a cartridge for receiving dry powder, and a powder dispersion mechanism comprising an energy source configured to generate and disperse a plume of powder particles having an average diameter of less than about 5-6 µm or a range of particle size that is consistent with the particle size distribution of the original powder formulation. In certain embodiments, at least 70% of the generated particles have a diameter of less than about 5-6 µm.

In certain embodiments, the powder dispersion mechanism and/or energy source configured to generate and disperse the plume of powder particles may be activated by at least one differential pressure sensor located within the housing of the dry powder delivery device upon sensing a pre-determined pressure change within the housing. In certain embodiments, such a pre-determined pressure change may be sensed during an inspiration cycle by a user of the device, as will be explained in further detail herein.

In a further aspect, the disclosure relates to a breath actuated dry powder delivery device for delivering a powder drug formulation as a generated plume of particles for delivery to the pulmonary system of a subject. In certain embodiments, the breath actuated dry powder delivery device may include a housing comprising a mouthpiece located at an airflow exit side of the housing, and a laminar flow element; a cartridge disposed within or removably attached to the housing, for receiving a volume of powder; a powder dispersion mechanism, the powder dispersion comprising an energy source configured to generate and disperse a plume of particles from a powder received in the cartridge; and at least one differential pressure sensor positioned within the housing.

In certain embodiments, the cartridge of the dry powder delivery device may be configured as a single dose, a multi-dose or unit-dose unit, including a reusable or disposable powder reservoir, e.g., with factory metered and sealed doses that may be packaged so that the cartridge can hold a single dose or multiple doses at the same time without having to be reloaded. In certain embodiments, the cartridge may be a rotary device that is removable and coupled to the body of the dry powder delivery device. In yet other aspects, the reservoir/cartridge of the dry powder delivery device may be a removable and replaceable multi-unit dose or single-unit dose cartridge.

In certain embodiments, the device may include: a housing; a multi-unit dose or single-unit dose reservoir/cartridge for receiving a dry powder; at least one differential pressure sensor positioned within the housing; and a powder dispersion generating mechanism comprising of an energy source such as a compressed gas source, e.g., a $CO_2$ compressed gas source cartridge, that is activated by the at least one differential pressure sensor to disperse the dry powder included in the multi-unit dose or single-unit dose cartridge as a plume of particles of powder. The reservoir/cartridge for receiving the dry powder may be located within the housing or may removably attached to the housing, as described in further detail herein.

By way of example, the at least one differential pressure sensor may be configured to activate the rotation of the multi-unit dose/single-unit dose cartridge to expose a dose of dry powder to a jet stream of compressed gas such as $CO_2$ gas. The powder dispersion generating mechanism may be activated by the at least one differential pressure sensor so as to generate sufficiently high shear force to deagglomerate and disperse the dry powder contained in the multi-unit dose or single-unit dose cartridge as an plume of particles of particles.

In certain embodiments, the powder dispersion generating mechanism may be activated upon sensing a pre-determined pressure change within the housing when a subject applies an inspiratory breath to an airflow exit side of the housing. The powder dispersion generating mechanism may be configured to generate a plume of particles of dry powder wherein at least about 70% of the plume of particles have an average particle diameter of less than about 5 microns, such that at least about 70% of the plume of particles are delivered in a respirable range to the pulmonary system of the subject during use.

In some aspects, the dry powder delivery device further includes a laminar flow element located at the airflow entrance side of the housing and configured to facilitate substantial laminar airflow across the exit side of the generated powder stream and to provide sufficient airflow to ensure that the stream of powder particles flows through the device during use. In certain aspects, the substantial laminar airflow includes airflow that is generally laminar without turbulent mixing zones. However, in some embodiments, it may be desirable to design the interior of the dry powder delivery device to allow for a turbulent mixing zone below the exit side of the generated particle plume to facilitate deaggolmeration of the powder particles. In such embodiments, the dry powder delivery device may be configured without a laminar flow element.

In other aspects, the powder delivery device may further include a mouthpiece coupled with the housing generally opposite the laminar flow element. In certain embodiments, the mouthpiece may be removable and/or replaceable, e.g., to facilitate cleaning of the dry powder delivery device.

In other aspects, the dry powder delivery device may further include a wireless communication module. In some aspects, the wireless communication module is a Bluetooth transmitter.

In yet other aspects, the dry powder delivery device may further include one or more sensors selected from an inferred transmitter, a photodetector, an additional pressure sensor, and combinations thereof.

In other aspects the port or orifice through which the plume of particles is generated is orientated with reference to the housing such that the generated plume of particles are directed into and through the housing at an approximate 90 degree change of trajectory prior to expulsion from the housing.

In a further aspect, this disclosure relates to a method of filtering large particle aggregates from a plume of particles of dry powder using inertial forces. The method may include: generating a plume of particles of dry powder using a dry powder delivery device described herein, wherein the dry powder generating mechanism is orientated with reference to the housing such that the plume of particles is directed into and through the housing at an approximate 90 degree change of trajectory prior to expulsion from the housing; and wherein the particles of dry powder having a diameter greater than about 5 μm are deposited on the sidewalls of the housing due to inertial forces, without being carried in entrained airflow through and out of the dry powder delivery device to the pulmonary system of the subject.

In certain aspects, the present disclosure relates to a dry powder delivery device for delivering a dry powder as a plume of particles to the pulmonary system of a subject. In certain aspects, the therapeutic agents may be delivered at a high dose concentration and efficacy, as compared to alternative dosing routes and standard inhalation technologies.

In certain embodiments, the dry powder delivery devices of the disclosure may be used to treat various diseases, disorders and conditions by delivering therapeutic agents to the pulmonary system of a subject. In this regard, the particle delivery devices may be used to deliver therapeutic agents both locally to the pulmonary system, and systemically to the body.

More specifically, the dry powder delivery device may be used to deliver therapeutic agents as a generated plume of particles to the pulmonary system of a subject for the treatment or prevention of pulmonary diseases or disorders such as (COPD) cystic fibrosis (CF), tuberculosis, chronic bronchitis, or pneumonia. In certain embodiments, the dry powder delivery device may be used to deliver therapeutic agents such as COPD medications, asthma medications, or antibiotics. By way of non-limiting example, such therapeutic agents include albuterol sulfate, ipratropium bromide, tobramycin, and combinations thereof.

In other embodiments, the dry powder delivery device may be used for the systemic delivery of therapeutic agents including small molecules, therapeutic peptides, proteins, antibodies, and other bioengineered molecules via the pulmonary system. By way of non-limiting example, the dry powder delivery device may be used to systemically deliver therapeutic agents for the treatment or prevention of indications inducing, e.g., diabetes mellitus, rheumatoid arthritis, plaque psoriasis, Crohn's disease, hormone replacement, neutropenia, nausea, influenza, etc.

By way of non-limiting example, therapeutic peptides, proteins, antibodies, and other bioengineered molecules include: growth factors, insulin, vaccines (Prevnor—Pneumonia, Gardasil—HPV), antibodies (Avastin, Humira, Remicade, Herceptin), Fc Fusion Proteins (Enbrel, Orencia), hormones (Elonva—long actin albuterol sulfate g FSH, Growth Hormone), enzymes (Pulmozyme—rHu-DNAase-), other proteins (Clotting factors, Interleukins, Albumin), gene therapy and RNAi, cell therapy (Provenge—Prostate cancer vaccine), antibody drug conjugates—Adcetris (Brentuximab vedotin for HL), cytokines, anti-infective agents, polynucleotides, oligonucleotides (e.g., gene vectors), or any combination thereof; or other solid particles or suspensions such as Flonase (fluticasone propionate) or Advair (fluticasone propionate and salmeterol xinafoate).

In certain embodiments, the dry powder delivery device of the disclosure may be used to deliver scheduled and controlled substances such as narcotics for the highly controlled dispense of pain medications where dosing is only enabled by doctor or pharmacy communication to the device, and where dosing may only be enabled in a specific location such as the patient's residence as verified by GPS location on the patient's smart phone. This mechanism of highly controlled dispensing of controlled medications can prevent the abuse or overdose of narcotics or other addictive drugs.

Certain benefits of the pulmonary route for delivery of drugs and other medications include a non-invasive, needle-free delivery system that is suitable for delivery of a wide range of substances from small molecules to very large proteins, reduced level of metabolizing enzymes compared to the GI tract and absorbed molecules do not undergo a first pass effect. (A. Tronde, et al., *J Pharm Sci*, 92 (2003) 1216-1233; A. L. Adjei, et al., Inhalation Delivery of Therapeutic Peptides and Proteins, M. Dekker, New York, 1997). Further, medications that are administered orally or intravenously are diluted through the body, while medications given directly into the lungs may provide concentrations at the target site (the lungs) that are about 100 times higher than the same intravenous dose. This is especially important for treatment of drug resistant bacteria, drug resistant tuberculosis, for example and to address drug resistant bacterial infections that are an increasing problem in the ICU.

Another benefit for giving medication directly into the lungs is that high, toxic levels of medications in the blood plume their associated side effects can be minimized. For example intravenous administration of tobramycin leads to very high serum levels that are toxic to the kidneys and therefore limits its use, while administration by inhalation significantly improves pulmonary function without severe side effects to kidney functions. (Ramsey et al., Intermittent administration of inhaled tobramycin in patients with cystic fibrosis. *N Engl J Med* 1999; 340:23-30; MacLusky et al., Long-term effects of inhaled tobramycin in patients with cystic fibrosis colonized with *Pseudomonas aeruginosa*. *Pediatr Pulmonol* 1989; 7:42-48; Geller et al., Pharmacokinetics and bioavailability of aerosolized tobramycin in cystic fibrosis. Chest 2002; 122:219-226.)

As discussed above, effective delivery of particles deep into the lung airways require particles that are less than about 5 microns in diameter, specifically particles with mass mean aerodynamic diameters (MMAD) that are less than about 5 microns. The mass mean aerodynamic diameter is defined as the diameter at which 50% of the particles by mass are larger and 50% are smaller. In certain aspects of the disclosure, in order to deposit in the alveolar airways, particles in this size range must have momentum that is sufficiently high to permit expulsion out of the device, but sufficiently low to overcome deposition onto the tongue (soft palate) or pharynx.

In other aspects of the disclosure, methods for generating a plume of particles for delivery to the pulmonary system of user using the dry particle delivery devices of the disclosure are provided. In certain embodiments, the plume of dry particles is generated in a controllable and defined particle size range. By way of example, the particle size range includes at least about 50%, at least about 60%, at least about 70%, at least about 85%, at least about 90%, between about 50% and about 90%, between about 60% and about 90%, between about 70% and about 90%, etc., of the generated particles are in the respirable range of below about 5 μm.

In other embodiments, the plume of particles may have one or more diameters, such that particles having multiple diameters are generated so as to target multiple regions in the airways (mouth, tongue, throat, upper airways, lower airways, deep lung, etc.) By way of example, particle diameters may range from about 1 μm to about 200 μm, about 2 μm to about 100 μm, about 2 μm to about 60 μm, about 2 μm to about 40 μm, about 2 μm to about 20 μm, about 1 μm to about 5 μm, about 1 μm to about 4.7 μm, about 1 μm to about 4 μm, about 10 μm to about 40 μm, about 10 μm to about 20 μm, about 5 μm to about 10 μm, and combinations thereof. In particular embodiments, at least a fraction of the particles have diameters in the respirable range, while other particles may have diameters in other sizes so as to target non-respirable locations (e.g., larger than 5 μm). Illustrative particle plumes in this regard might have 50%-70% of particles in the respirable range (less than about 5 μm), and 30%-50% outside of the respirable range (about 5 μm-about 10 μm, about 5 μm-about 20 μm, etc.)

In another embodiment, methods for delivering safe, suitable, and repeatable dosages of a medicament to the pulmonary system using the dry powder delivery devices of the disclosure are provided. The methods deliver a plume of particles to the desired location within the pulmonary system of the subject, including the deep lungs and alveolar airways.

In certain aspects of the disclosure, a dry powder delivery device for delivery a plume of particles to the pulmonary system of a subject is provided. The dry powder delivery device generally includes a housing and a reservoir or cartridge disposed in or in proximity to the housing for receiving dry powder, a powder dispersion mechanism in proximity with the reservoir or cartridge including an energy source, e.g., comprising a compressed gas such as $CO_2$ gas, and at least one differential pressure sensor positioned within the housing. The differential pressure sensor may be configured to activate the rotation of the reservoir or cartridge so as to expose a unit dose of dry powder, and to activate the powder dispersion mechanism to generate a jet spray of compressed gas to disperse/deagglomerate the dry powder, upon sensing a pre-determined pressure change within the housing. By way of example, in certain embodiments, the powder dispersion mechanism may be configured to generate a jet spray of compressed gas to thereby disperse/deagglomerate the dry powder and generate a controllable plume of particles of dry powder.

By way of non-limiting example, energy sources other than compressed gas may be used to disperse/deagglomerate the dry powder formulation. Without limitation, exemplary alternate energy sources include battery powered thermal vaporization, vibration using, e.g., a spring-loaded mechanism, acoustic, sonic or ultrasonic wave, piezoelectric-actuated membrane, or ultrasonic plate ejector system, laser ablation, etc. In certain embodiments, the powder dispersion mechanism may be configured to accommodate different therapeutic molecules with attributes more specific to their unique physicochemical properties. (D. C. Cipolla and I. Gonda, Formulation technology to repurpose drugs for inhalation delivery, *Drug Discov. Today: Ther. Strateg.*, 2011; 8(3-4): 123-130).

Reference will now be made to the figures, with like components illustrates with like references numbers.

Referring to FIG. 1A, in one aspect of the disclosure, a dry powder particle delivery device 100 is illustrated in use by a patient. Particle delivery device 100 may include one or more differential pressure sensors (not shown) to provide for automatic electronic breath actuation of the device. Such pressure sensor(s) automatically detects a desired point during a user's inhalation cycle to activate the actuation of the dry powder dispersal mechanism 104 to generate a plume of particles. For instance, a user may begin to inhale, pulling air through the back of the device at 1, triggering the differential pressure sensor and thereby activating actuation of a motor for cartridge rotation to expose a unit-dose of powder medication followed by generation of a jet of $CO_2$ gas stream to activate the powder dispersion mechanism 104 to generate a plume of particles at 2, which plume of particles are entrained in the user's inhalation airflow thereby traveling along the device and into the user's airway at 3. As will be explained in further detail herein, any large particles or particle aggregates are removed from the entrained airflow via inertial filtering, falling to the bottom surface of the device at 4. By way of non-limiting example, the pressure sensor(s) may be programmed to trigger a 2 second ejection of compressed $CO_2$ gas for dispersal of the dry powder when the user generated airflow within the device is about 10 SLM or similar pressure. However, any suitable differential pressure within a standard physiological range of a target user may be used. Such a trigger point during the inspiratory cycle may provide an optimum point during a user's inhalation cycle to activate and actuate the generation of a plume of particles, and delivery of medication. Since electronic breath actuation does not require user-device coordination, the particle delivery devices and methods of the disclosure further provide assurance for optimum delivery of inhaled medication.

As shown in FIG. 1A, the dry powder delivery device may include a housing that is configured to comprise a base handle and an inhalation piece, wherein the base handle includes, e.g., batteries and a compressed gas container, while the inhalation piece includes a mouthpiece, cartridge, laminar flow element, etc. (as described in further detail with reference to FIGS. 2A-2B, FIGS. 3A-3D, etc.). However, the disclosure is not so limited. For instance, in certain embodiments, the dry powder delivery device may be configured in an "in-line" orientation in that the primary components of the device, e.g. the dry powder dispersion mechanism and related sensors and electronic components, are packaged in a housing and oriented in a generally in-line or parallel configuration so as to form a small, hand-held device.

Figure 1B:
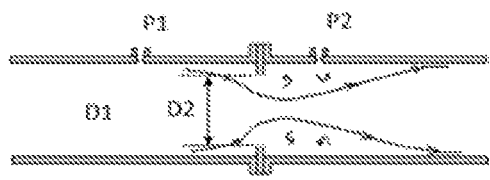
FIGS. 1B, 1C, and 1D illustrate an example of an inhalation detection system that senses airflow by detecting pressure differentials across flow restriction, in accordance with embodiments of the disclosure.
Figure 1C:
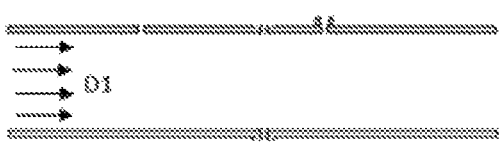

By way of non-limiting example, FIGS. 1B-1E illustrate inhalation detection systems according to embodiments of the disclosure that sense airflow by detecting pressure differentials across a flow restriction. Referring to FIGS. 1B-E, dry powder delivery device configurations of disclosure are providing including various sensor orientation that provide for automatic breath actuation of the dry powder dispersion mechanism and automatic spray verification. The sensors trigger actuation of a plume during a peak period of a patient's inhalation cycle. In certain implementations the coordination of a patient's peak period of inhalation may assure optimum deposition of the plume and associated drug delivery into the pulmonary airways of the patient. Although a number of arrangements are possible, FIG. 1B shows an exemplary sensor configuration. SDPx series (SDP31 or SDP32 pressure sensors) from Sensirion (www.sensirion.com) may be used.

Figure 1D:
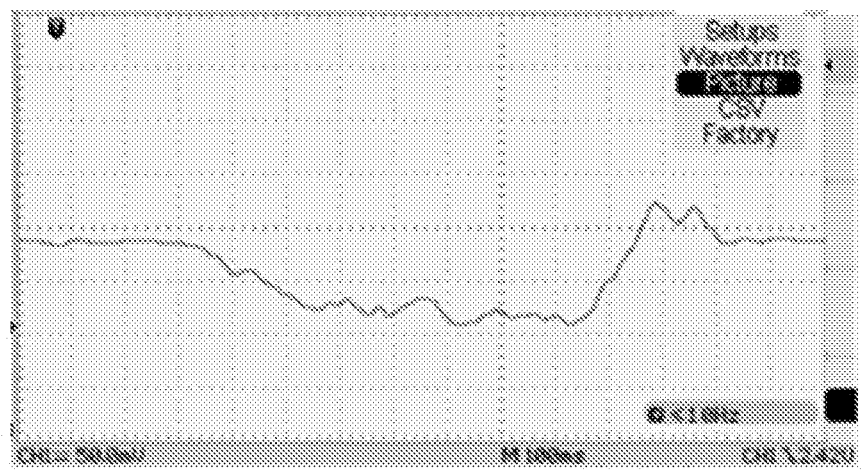
Figure 1E:
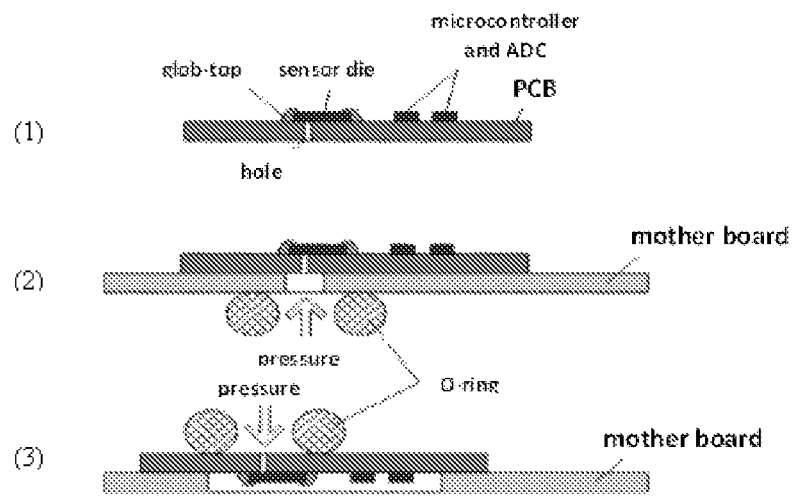
FIG. 1E illustrates exemplary delta P sensor design and its assembly onto a device board: (1). The sensor has pneumatic connection through the hole in the printed circuit board (PCB) and may be mounted either on the main PCB as shown on schemes (2) or on a daughter board on scheme (3).

As will be discussed in further detail below, e.g., with reference to FIGS. 2A-2B, one or more pressure sensors may be located within the dry powder delivery device of the disclosure within a restriction that is internal to the device, e.g., within the delivery mouthpiece tube. For instance, FIG. 1B is an example where the restriction is internal to the device tube, and FIG. 1C, the restriction is at the air inlet laminar flow element. The pressure is sensed as the differential between the interior of the device tube and the pressure outside the tube. FIG. 1D is a screen capture of an exemplary pressure sensor response to an inhaled breath of a ~1 second duration. FIG. 1E illustrates exemplary differential pressure sensor designs and assemblies onto a device board (1). The sensor may have pneumatic connection through the hole in the printed circuit board (PCB) and may be mounted either on the main PCB, as shown below on scheme (2), or on a daughter board as shown on scheme (3).

Figure 2A:
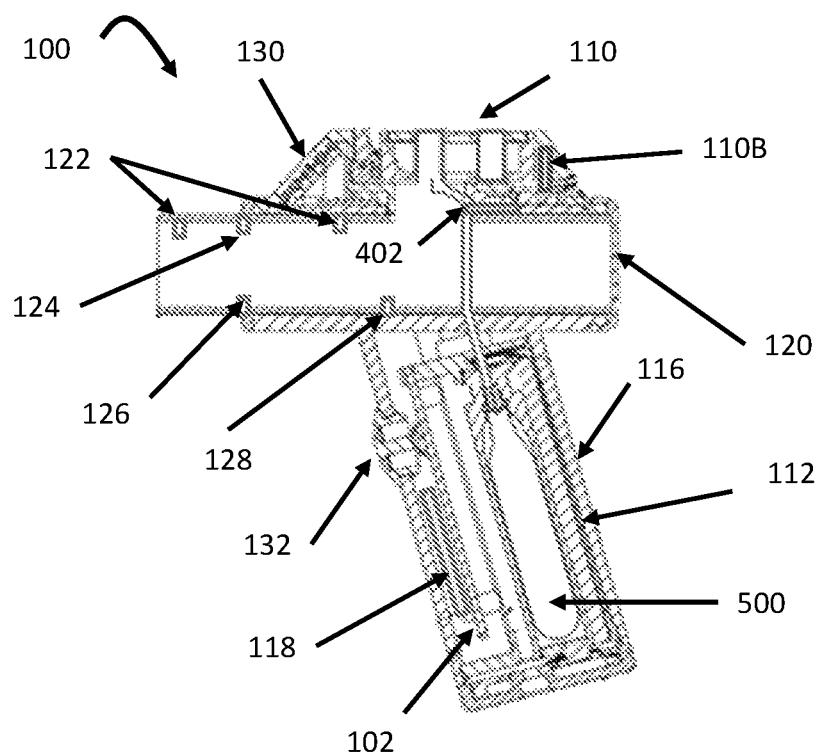
FIG. 2A is a cross section view of a dry powder delivery device in accordance with an embodiment of the disclosure.

In one embodiment, referring to FIG. 2A, an exemplary dry powder delivery device 100 is illustrated including a power/activation button 132; an electronics circuit board 102; a dry powder dispersion mechanism which, by way of example may include a gas (e.g., $CO_2$) cartridge 500 to disperse powder formulations and a valve 402 that is breath actuated; a cartridge or reservoir 110 that may contain single-unit dose or multi-unit dose that may be rotated by a gear motor 110B to expose the unit dose for deagglomeration/particle generation; and a device power source 112 (which may optionally be rechargeable) electronically coupled to the gear motor 110B and valve 402. In certain embodiments, the cartridge/reservoir 110 may be single-unit dose or multi-unit dose that may be replaceable, disposable or reusable.

Dry powder delivery device 100 includes power source 112, which when activated, e.g., by one or more pressure sensors 122 upon sensing a pre-determined change in pressure within the device, will energize the gear motor 110B and valve 402 to rotate the cartridge/reservoir 110 to expose a unit dose of dry powder formulation and to deagglomerate and generate a plume of dry powder particles to be generated.

The components may be packaged in a housing 116, which may be disposable or reusable, single-dose or multi-dose. The housing 116 may be handheld. In certain embodiments, as illustrated, the housing may be configured with a base handle and inhalation portion. In other embodiments (not shown), the housing may be configured in an "in-line"

configuration that is generally oriented in an in-line or parallel configuration so as to form a small, hand-held device.

In certain embodiments, the housing 116 may be adapted for communication with other devices via a Bluetooth® or other wireless communication module 118, e.g., for communication with a subject's smart phone, tablet or smart device (not shown). In one embodiment, laminar flow element 120 may be located at the air entry side of the housing 116 to facilitate substantial laminar airflow across the exit side of the dry powder dispersion mechanism, and to provide sufficient airflow to ensure that the plume of particles flow through the device during use. Aspects of the present embodiment further allows customizing the internal pressure resistance of the particle delivery device by allowing the placement of laminar flow elements having openings of different sizes and varying configurations to selectively increase or decrease internal pressure resistance, as will be explained in further detail herein.

Particle delivery device 100 may further include various sensors and detectors 122, 124, 126, and 128 to facilitate device activation, spray verification, patient compliance, diagnostic mechanisms, or as part of a larger network for data storage, big data analytics and for interacting and interconnected devices used for subject care and treatment, as described further herein. Further, housing 116 may include an LED assembly 130 on a surface thereof to indicate various status notifications, e.g., ON/READY, ERROR, etc.

The airflow exit of housing 116 of the dry particle delivery device 100 of FIG. 2A through which the plume of particles exit as they are inhaled into a subject's airways, may be configured and have, without limitation, a cross sectional shape of a circle, oval, rectangular, hexagonal or other shape, while the shape of the length of the tube, again without limitation, may be straight, curved or have a Venturi-type shape.

In another embodiment (not shown), a mini fan or centrifugal blower may be located at the air inlet side of the laminar flow element 120 or internally of the housing 116 within the airsteam. The mini fan generally may provide additional airflow and pressure to the output of the plume. For patients with low pulmonary output, this additional airplume may ensure that the plume of particles is pushed through the device into the patient's airway. In certain implementations, this additional source of airflow ensures that the plume exit port is swept clean of the particles and also provides mechanism for spreading the particle plume into an airflow which creates greater separation between particles. The airflow provided by the mini fan may also act as a carrier gas, ensuring adequate dose dilution and delivery.

Figure 2B:
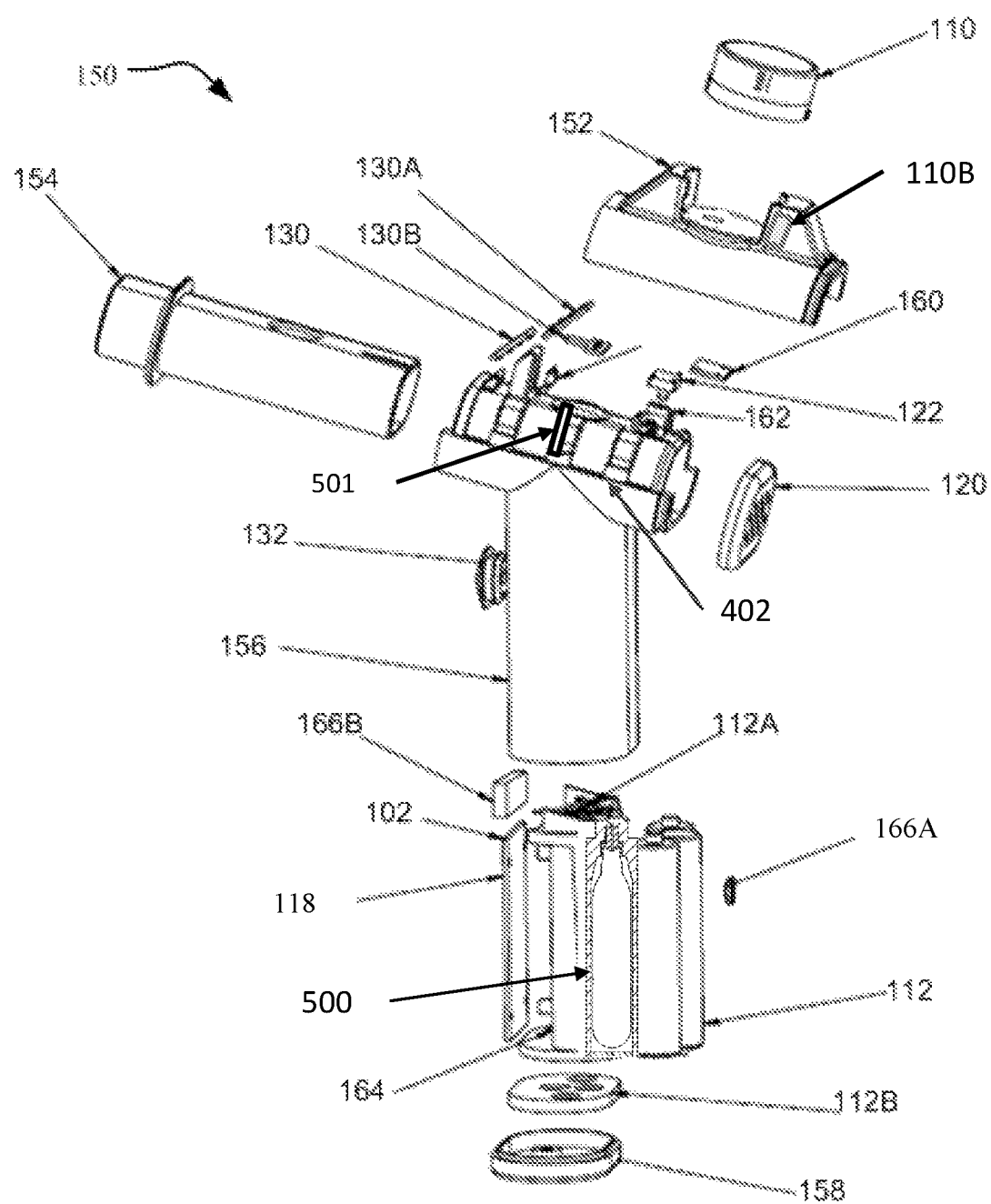
FIG. 2B is an exploded view of the droplet delivery device of FIG. 2A.

With reference to FIG. 2B, a dry particle delivery device of the disclosure is illustrated in an exploded view. Again, like components are indicated with like reference numbers. Dry Powder delivery device 150 is illustrated with a top cover 152, which provides a cover for the delivery mouthpiece tube 154 and interfaces with cartridge/reservoir 110, a base handle 156, an activation button 132, and bottom cover for the handle 158.

A series of colored lights powered by an LED assembly are located in the front region of the dry powder delivery device. In this embodiment, the LED assembly 130, including, e.g., four LED's, 130A, 130B, and an electronics board 130B, on which the LED assembly 130 is mounted and provides an electrical connection to the main electronics board 102. The LED assembly 130 may provide the user with immediate feedback on functions such as, power, ON and OFF, to signal when breath activation occurs (as described further herein), to provide the user with feedback as to when an effective or ineffective dispense of a dose is delivered (as described further herein), or to provide other user feedback to maximize patient compliance.

The laminar flow element 120 may be located opposite the patient use end of the mouthpiece tube 154, and a differential pressure sensor 122, pressure sensor electronics board 160, and pressure sensor O-ring 162 are located nearby. In certain embodiments (not shown), the laminar flow element may be located internal to the inhalation or mouthpiece tube, opposite the patient use end and prior to the air intake zone of the inhalation or mouthpiece tube.

The remaining components detailed in FIG. 2B may be located in the base handle 156, which include the mount assembly 164 for device power source 112 (e.g., three, AAA batteries), top and bottom battery contacts, 112A, 112B, and audio chip and speaker, 166A and 166B. However, as described herein, in certain embodiments (not shown), the dry powder delivery device of the disclosure may be configured in an "in-line" configuration that is generally oriented in an in-line or parallel configuration so as to form a small, hand-held device.

Again, with reference to FIG. 2B, a Bluetooth communication module 118 or similar wireless communication module is provided in order to link the particle delivery device 150 to a smartphone or other similar smart devices (not shown). Bluetooth connectivity facilitates implementation of various software or App's which may provide and facilitate patient training on the use of the device. A major obstacle to effective inhaler drug therapy has been either poor patient adherence to prescribed aerosol therapy or errors in the use of an inhaler device. By providing a real time display on the smartphone screen of a plot of the patient's inspiratory cycle, (flow rate versus time) and total volume, the patient may be challenged to reach a goal of total inspiratory volume that was previously established and recorded on the smartphone during a training session in a doctor's office. Bluetooth connectivity further facilitates patient adherence to prescribed drug therapy and promotes compliance by providing a means of storing and archiving compliance information, or diagnostic data (either on the smartphone or cloud or other large network of data storage) that may be used for patient care and treatment.

More specifically, in certain embodiments, the dry particle delivery device may provide automatic spray verification via LED and photodetector mechanisms. With reference to FIGS. 2A-2B, an infra-red transmitter (e.g., IR LED, or UV LED <280 nm LED), 126 and infra-red or UV (UV with <280 nm cutoff) photodetector 124 may be mounted along the particle generation side of the device to transmit an infra-red or UV beam or pulse, which detects the plume of particles and thereby may be used for spray detection and verification. The IR or UV signal interacts with the aerosol plume and can be used to verify that a plume of particles has been generated as well as provide a measure of the corresponding dispersed dose of medicament. Examples include but not limited to, infrared 850 nm emitters with narrow viewing angles of either, 8, 10 and 12-degrees, (MTE2087 series) or 275 nm UV LED with a GaN photodetector for aerosol plume verification in the solar blind region of the spectra. Alternatively in some applications, the sub 280 nm LEDs (e.g. 260 nm LEDs) can be used to disinfect the spacer tube 128.

The particle delivery mouthpiece tube 154 may be removable, replaceable and sterilizable. This feature improves sanitation for drug delivery by providing means and ways to minimize buildup of aerosolized medication within the mouthpiece tube by providing ease of replacement, disinfection and washing. In one embodiment, the mouthpiece tube may be formed using sterilizable and transparent polymer compositions such as polycarbonate, polyethylene or polypropylene, and not limited by example.

Figure 2C:
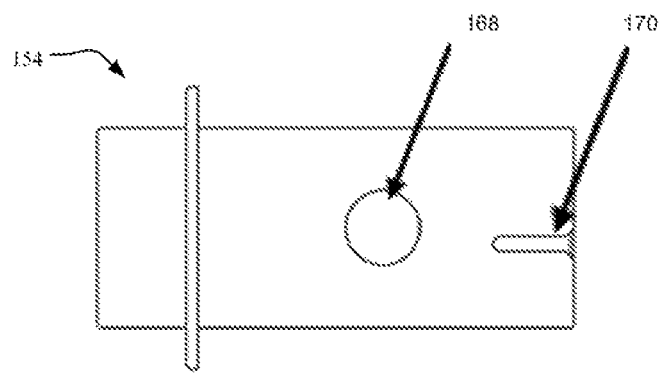
FIG. 2C is a top view of a mouthpiece tube, in accordance with an embodiment of the disclosure.

With reference to FIG. 2C, a top view of an exemplary delivery mouthpiece tube 154 is illustrated, which includes a circular port 168 through which the plume passes from the powder dispersion mechanism (not shown), as well as the location of a slot 170 that accommodates the pressure sensor (not shown). Materials selection for the delivery mouthpiece tube should generally allow effective cleaning and have electrostatic properties that do not interfere with or trap powder particles of interest. Unlike many dry powder devices with larger particles and higher dispense velocities, the mouthpiece of the disclosure does not need to be long or specially shaped to reduce the speed of large particles that would otherwise impact the back of the patients mouth and throat.

Figure 2D:
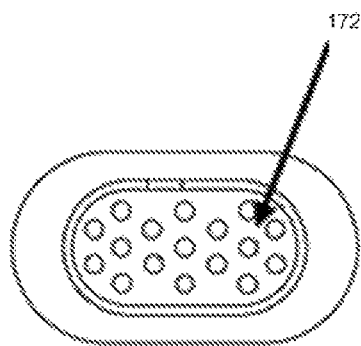
FIG. 2D is a front view of a mouthpiece tube with an air aperture grid or opening, in accordance with an embodiment of the disclosure.

In other embodiments, the internal pressure resistance of the dry powder delivery device may be customized to an individual user or user group by modifying the mouthpiece tube design to include various configurations of air aperture grids or openings, thereby increasing or decreasing resistance to airflow through the device as the user inhales. For instance, with reference to FIG. 2D, an exemplary aperture grid 172 at the mouthpiece tube opening is illustrated. However, different air entrance aperture sizes and numbers may be used to achieve different resistance values, and thereby different internal device pressure values. This feature provides a mechanism to easily and quickly adapt and customize the airway resistance of the particle delivery device to the individual patient's state of health or condition.

With reference to FIGS. 3A-3D, an embodiment of the disclosure is illustrated showing a dry powder delivery device of the disclosure including a rotatable cartridge comprising a number of blister elements for holding dry powder medicaments for delivery to a user upon actuation of the device. Once activated, the dry powder delivery device of the disclosure may be actuated to deliver a plume of particles for any suitable time sufficient to deliver a unit dose contained within one of the cartridge blister element. FIG. 3A illustrates a cross-sectional side view of an exemplary dry powder delivery device according to an embodiment of the disclosure. FIG. 3B illustrates a cross-sectional side view of a cartridge/reservoir 110, in accordance with an embodiment of the disclosure. FIG. 3C illustrates a top view of a rotatable cartridge that contains 12 blister elements 110A. A geared motor mechanism 110B (such as model ZWPD006006 from Zhao Wei Enterprise, FIG. 44B illustrate exemplary operating parameters and component specifications) may be used to rotate the cartridge 110 to the next blister element 110A before a jet of $CO_2$ gas stream through gas dispersal element 501 from gas container 500 via valve 402 may be used to disperse the dry powder. As shown in FIG. 3D, a stationary plate 110C which covers the bottom of the cartridge element may provide a seal for the blister elements 110A such that a single blister element is exposed for $CO_2$ dispersal when the cartridge is rotated to the open port 502, as a result of breath actuation for delivery of the next dose.

Figure 3E:
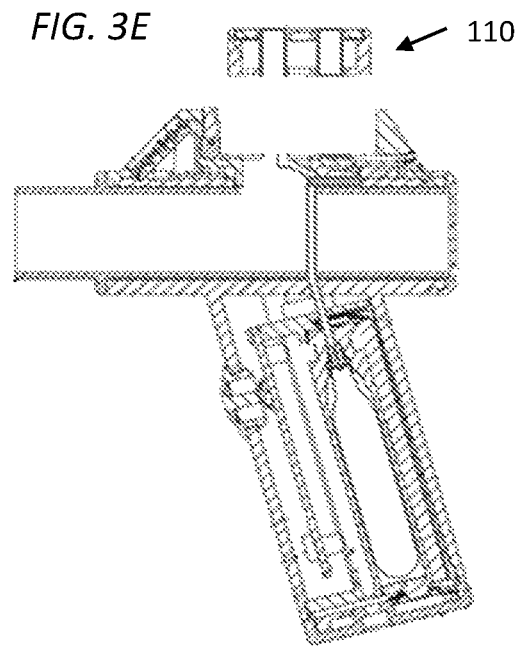
FIGS. 3E-3G illustrate activation of a dry powder delivery device in accordance with an embodiment of the disclosure, with FIG. 3E showing insertion of a rotatable cartridge/reservoir and cover disk, FIGS. 3F and 3G showing activation of valve and motor to cause a jet of $CO_2$ gas to generate a plume of dry powder.
Figure 3F:
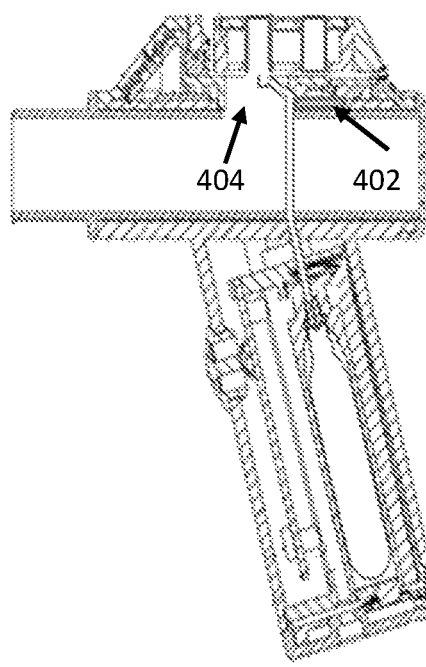
Figure 3G:
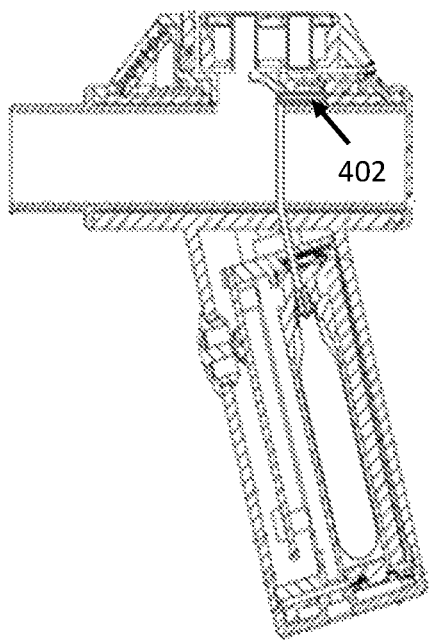

In certain aspects, as illustrated in FIGS. 3E-3G the differential pressure sensor is configured to activate both the rotation of the cartridge 110 so as to expose a unit dose of dry powder formulation 110A to a jet spray of compressed $CO_2$ gas and actuate a valve mechanism 402 that is operated by, e.g., a piezo-driven squiggle motor 404 (such as SQL-RV-1.8 from NewScale Technologies, (NewScale Tech.com)), in order to release the jet spray of compressed $CO_2$ gas. This sequence of action provides a powder dispersion mechanism to generate a plume of particles upon sensing a pre-determined pressure change within the housing.

For instance, the cartridge mechanism may be activated to rotate so as to expose a unit dose of dry powder formulation to a jet of compressed $CO_2$ gas to thereby generate the plume of particles for a short burst of time, e.g., one tenth of a second, or for several seconds, e.g., 5 seconds. In certain embodiments, the dry powder delivery device may be activated to generate and deliver the plume of particles, e.g., for up to about 5 seconds, up to about 4 seconds, up to about 3 seconds, up to about 2 seconds, up to about 1 second, between about 1 second and about 2 seconds, between about 0.5 seconds and 2 seconds, etc.

In certain embodiments, any suitable differential pressure sensor with adequate sensitivity to measure pressure changes obtained during standard inhalation cycles may be used, e.g., ±5 SLM, 10 SLM, 20 SLM, etc. For instance, pressure sensors from Sensirion, Inc., SDP31 or SDP32 (U.S. Pat. No. 7,490,511 B2) are particularly well suited for these applications.

In certain embodiments of the present disclosure, the signal generated by the pressure sensors provides a trigger for activation and actuation of the mechanism for cartridge rotation and $CO_2$ jet generation of the dry powder delivery device at or during a peak period of a patient's inhalation (inspiratory) cycle and assures optimum deposition of the plume of particles and delivery of the medication into the pulmonary airways of the user.

In addition, an image capture device, including cameras, scanners, or other sensors without limitation, e.g. charge coupled device (CCD), may be provided to detect and measure the particle plume. These detectors, LED, delta P transducer, CCD device, all provide controlling signals to a microprocessor or controller in the device used for monitoring, sensing, measuring and controlling the generation of a plume of particles and reporting patient compliance, treatment times, dosage, and patient usage history, etc., via Bluetooth, for example.

In certain aspects of the disclosure, the powder dispersion mechanism, cartridge/reservoir, and housing/mouthpiece function to generate a plume with average particle diameters less than about 5-6 µm. As discussed above, in certain embodiments, the cartridge/reservoir and powder dispersion mechanism modules are powered by electronics in the device housing and a dry powder cartridge/reservoir which may carry sufficient drug for a single dose, just a few doses, or several hundred doses of medicament.

In certain embodiments, as illustrated herein, the cartridge/reservoir module may include components that may carry information read by the housing electronics including key parameters such as powder dispersion mechanism functionality, drug identification, and information pertaining to patient dosing intervals. Some information may be added to the module at the factory, and some may be added at the pharmacy. In certain embodiments, information placed by the factory may be protected from modification by the pharmacy. The module information may be carried as a printed barcode or physical barcode encoded into the module geometry (such as light transmitting holes on a flange which are read by sensors on the housing). Information may also be carried by a programmable or non-programmable microchip on the module which communicates to the electronics in the housing.

By way of example, module programming at the factory or pharmacy may include a drug code which may be read by the device, communicated via Bluetooth® or other wireless communication module to an associated user smartphone and then verified as correct for the user. In the event a user inserts an incorrect, generic, damaged, etc., module into the device, the smartphone might be prompted to lock out operation of the device, thus providing a measure of user safety and security not possible with passive inhaler devices. In other embodiments, the device electronics can restrict use to a limited time period (perhaps a day, or weeks or months) to avoid issues related to drug aging or build-up of contamination or particulates within the device housing.

In certain embodiments, an airflow sensor may be located in the device delivery tube to, e.g., measure the inspiratory and expiratory flow rates flowing in and out of the mouthpiece. This sensor may be placed so that it does not interfere with drug delivery or become a site for collection of residue or promote bacterial growth or contamination. A differential (or gage) pressure sensor downplume of a flow restrictor (e.g., laminar flow element) may measure airflow based upon the pressure differential between the inside of the mouthpiece relative to the outside air pressure. During inhalation (inspiratory flow) the mouthpiece pressure will be lower than the ambient pressure and during exhalation (expiratory flow) the mouthpiece pressure will be greater than the ambient pressure. The magnitude of the pressure differential during an inspiratory cycle is a measure of the magnitude of airflow and airway resistance at the air inlet end of the delivery tube.

Any suitable material may be used to form the housing of the particle delivery device. In particular embodiment, the material should be selected such that it does not interact with the components of the device or the particle plume (e.g., drug or medicament components). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc.

In certain aspects of the disclosure, an electrostatic coating may be applied to the one or more portions of the housing, e.g., inner surfaces of the housing along the airflow pathway, to aid in reducing deposition of particles during use due to electrostatic charge build-up. Alternatively, one or more portions of the housing may be formed from a charge-dissipative polymer. For instance, conductive fillers are commercially available and may be compounded into the more common polymers used in medical applications, for example, PEEK, polycarbonate, polyolefins (polypropylene or polyethylene), or styrenes such as polystyrene or acrylic-butadiene-styrene (ABS) copolymers.

As described herein, the dry powder delivery device of the disclosure generally may include a laminar flow element located at the air entry side of the housing. The laminar flow element, in part, facilitates substantial laminar airflow across the aerosol plume exit port and provides sufficient airflow to ensure that the plume of particles flows through the particle delivery device during use. In addition, the laminar flow element allows for customization of internal device pressure resistance by designing openings of different sizes and varying configurations to selectively increase or decrease internal pressure resistance. In certain aspects, the substantial laminar airflow includes airflow that is generally laminar without turbulent mixing zones. However, in some embodiments, it may be desirable to design the interior of the dry powder delivery device to allow for a turbulent mixing zone below the exit side of the particle plume to facilitate deaggolmeration of the powder particles. In such embodiments, the dry powder delivery device may be configured without a laminar flow element.

In certain embodiments, the laminar flow element is designed and configured in order to provide an optimum airway resistance for achieving peak inspirational flows that are required for deep inhalation which promotes delivery of particles deep into the pulmonary airways. Laminar flow elements also function to promote substantial laminar flow across the particle plume exit port, which also serves to stabilize airflow repeatability, stability and insures an optimal precision in the delivered dose.

Without intending to be limited by theory, in accordance with aspects of the disclosure, the size, number, shape and orientation of holes in the laminar flow element of the disclosure may be configured to provide a desired pressure drop within the particle delivery device. In certain embodiments, it may be generally desirable to provide a pressure drop that is not so large as to strongly affect a user's breathing or perception of breathing.

Figure 4:
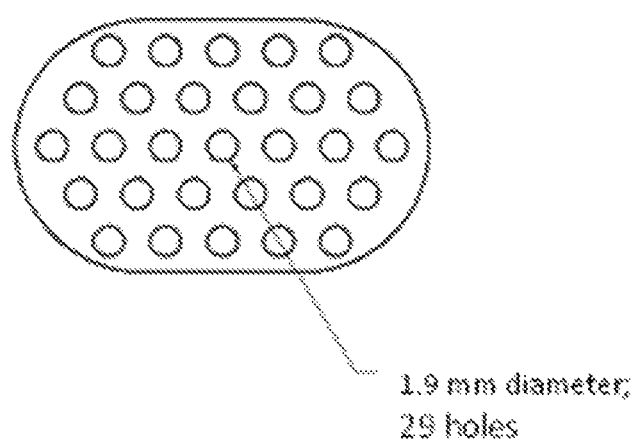
FIG. 4 illustrates an exemplary air inlet laminar flow screen with 29 holes, each 1.9 mm in diameter in accordance with an embodiment of the disclosure.

As illustrated in FIG. 4, a non-limiting exemplary laminar flow element may have 29 holes, each 1.9 mm in diameter. However, the disclosure is not so limited. For example, the laminar flow element may have hole diameters ranging from, e.g., 0.1 mm in diameter to diameters equal to the cross sectional diameter of the air inlet tube (e.g., 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, etc.), and number of holes may range from 1 to the number of holes, for example, to fill the laminar flow element area (e.g., 30, 60, 90, 100, 150, etc.). The laminar flow element may be mounted at the air inlet side of a particle delivery device as described herein.

In certain implementations, the use of laminar flow elements having different sized holes, or the use of adjustable apertures may be required in order to accommodate the differences among the lungs and associated inspiratory flow rates of young and old, small and large, and various pulmonary disease states. For example, if the aperture is adjustable by the patient (perhaps by having a slotted ring that can be rotated), then a method may be provided to read the aperture hole setting and lock that position to avoid inadvertent changes of the aperture hole size, hence the flow measurement. Although pressure sensing is an accurate method for flow measurement, other embodiments may use, e.g., hot wires or thermistor types of flow rate measurement methods which lose heat at a rate proportional to flow rate, moving blades (turbine flow meter technology) or by using a spring-loaded plate, without limitation of example.

Another aspect of the present disclosure as described herein, provides dry powder delivery device configurations and methods to increase the respirable dose of an generated plume of particles by filtering and excluding larger particles or particle aggregates (having a MMAD larger than 25 about 5 μm) from the aerosol plume by virtue of their higher inertial force and momentum (referred to herein as "inertial filtering"). In the event that droplet particles having MMAD larger than 5 μm are generated, their increased inertial mass may provide a means of excluding these larger particles from the airstream by deposition onto the mouthpiece of the droplet delivery device. This inertial filter effect of the drug delivery device of the disclosure further increases the respirable dose provided by the device, thus providing improved targeting delivery of medication to desired regions of the airways during use.

Without intending to be limited by theory, particles have an initial momentum that is large enough to be carried by the plume emerging from device. When a gas stream changes direction as it flows around an object in its path, suspended particles tend to keep moving in their original direction due to their inertia. However, particles having MMAD larger than 5 µm generally have a momentum that is sufficiently large to deposit onto the sidewall of the mouthpiece tube (due to their inertial mass), instead of being deflected and carried into the airflow.

Inertial mass is a measure of an object's resistance to acceleration when a force is applied. It is determined by applying a force to an object and measuring the acceleration that results from that force. An object with small inertial mass will accelerate more than an object with large inertial mass when acted upon by the same force.

To determine the inertial mass of a droplet particle, a force of F, Newtons is applied to an object, and the acceleration in m/s2 is measured. Inertial mass, m, is force per acceleration, in kilograms. Inertial force, as the name implies is the force due to the momentum of the droplets. This is usually expressed in the momentum equation by the term (ρv)v. So, the denser a fluid, and the higher its velocity, the more momentum (inertia) it has.

$$P = \frac{\pi \rho V d^3}{6}$$

$$F = \frac{d(mv)}{dt}$$

| | | |
|---|---|---|
| Momentum—p<br>The product of the mass and velocity is known as the linear momentum. | $p = m \cdot v \; \left[ kg \frac{m}{s} \right]$<br><br>The first derivation of the momentum with time is Force<br><br>$F = \frac{d(mv)}{dt}$<br><br>If m = m(t) and v = v(t)<br>then the derivation is:<br><br>$F = \frac{dm}{dt} v + m \frac{dv}{dt} = \frac{dm}{dt} v + m \cdot a$ | $N \cdot s$ |
| Angular Momentum—L | $L = I \cdot \omega \; \left[ kg \frac{m^2}{s} \right] = [N \cdot m \cdot s] = \frac{J}{s}$<br><br>I—Moment of inertia | $\frac{J}{s}$ |

Figure 5A:
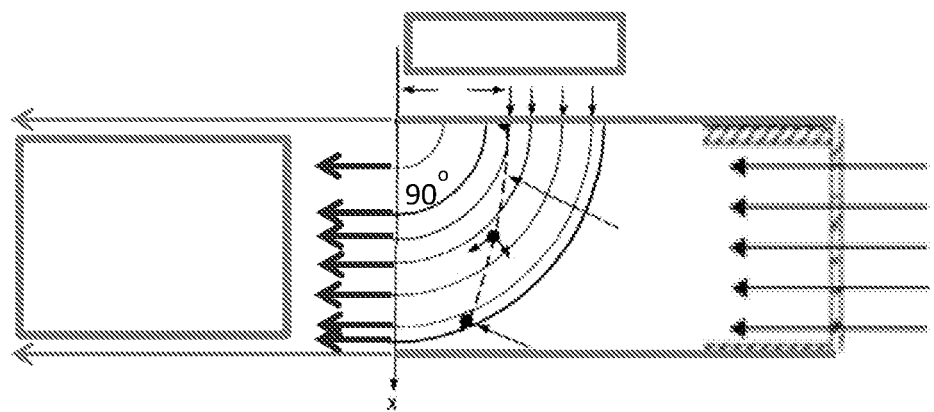
FIGS. 5A-5B depict inertial filter with a mechanism to select droplet size distribution by varying droplet exit angle, with FIG. 5A illustrating a 90 degree angle, and FIG. 5B illustrating an angle of larger than 90 degrees in accordance with embodiments of the disclosure.
Figure 5B:
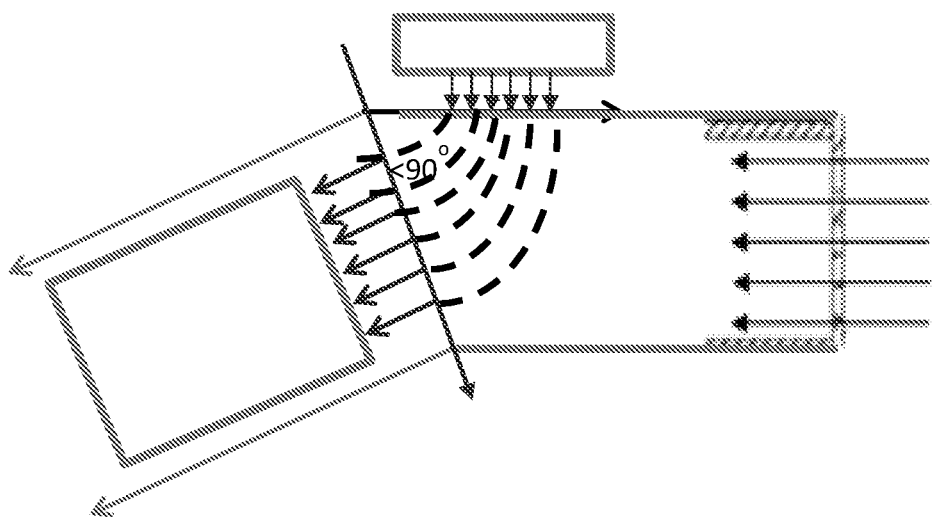

FIGS. 5A-5B illustrates inertial filtering provided by an exemplary dry powder delivery device of the disclosure for filtering and excluding larger particles and aggregates from the aerosol plume. Droplets undergo a 90 degree change in spray direction (4, 5) as particles emerge from the dry powder dispersion mechanism and are swept by the airflow (3) through the laminar flow element before inhalation into the pulmonary airways. Larger particles and aggregates above 5 µm (6) are deposited on the sidewall of the mouthpiece tube via inertial filtering.

In certain embodiments, larger particles and aggregates may be allowed to pass through the dry powder delivery device within the effects of inertial filtering or with varied effects of inertial filtering. For instance, the incoming airstream velocity may be increased (e.g., through use of the mini-fan described herein) so larger droplet particles may be carried into the pulmonary airways. Alternatively, the exit angle of the mouthpiece tube may be varied (increased or decreased) to allow for deposition of particles and aggregates of varying sizes on the sidewalls of the mouthpiece. By way of example, with reference to FIGS. 5A-5B, if the angle of the mouthpiece is changed, the larger or smaller particles will deposit or pass through the mouthpiece with or without impacting on the sidewalls of the mouthpiece. FIG. 5A illustrates an embodiment with a standard 90 degree turn, while FIG. 5B illustrate a greater than 90 degree turn. The embodiment of FIG. 5B would allow particles having a slightly larger diameter to pass without impacting on the sidewall of the mouthpiece.

In another aspect of the disclosure, in certain embodiments, the dry powder delivery devices provide for various automation, monitoring and diagnostic functions. By way of example, as described above, device actuation may be provided by way of automatic subject breath actuation. Further, in certain embodiments, the device may provide automatic spray verification, to ensure that the device has generated the proper particle generation and provided to proper dosing to the subject. In this regard, the particle delivery device may be provided with one or more sensors to facilitate such functionality.

In another aspect of the disclosure, the particle delivery device may be used in connection with or integrated with breathing assist devices such as a mechanical ventilator or portable Continuous Positive Airway Pressure (CPAP) machine, to provide in-line dosing of therapeutic agents with the breathing assistance airflow.

For example, mechanical ventilators with endo-tracheal (ET) tubes are used to block secretions from entering the lungs of an unconscious patient and/or to breathe for the patient. The ET tube seals to the inside of the trachea just below the larynx with an inflatable balloon. However, common undesirable side-effects that result from use of mechanical ventilators include ventilator-assisted pneumonia (VAP), which occurs in about ⅓ of patients who are on ventilators for 48 hours or more. As a result, VAP is associated with high morbidity (20% to 30%) and increased health care systems costs. (Fernando, et al., Nebulized antibiotics for ventilation-associated pneumonia: a systematic review and meta-analysis. *Critical Care* 19:150 2015).

Tobramycin administration through the pulmonary route is generally regarded as superior to intravenous administration for treating VAP, with nebulizers being typically used to deliver the antibiotics through generation of a continuous plume of particles into the ventilator airflow. The main benefit of inhaled versus oral or intravenous administered antibiotics is the ability to deliver a higher concentration of the antibiotic directly into the lungs. However, continuous generation of nebulizer mist provides imprecise dosing that cannot be verified between inhalation and exhalation cycles.

Figure 6:
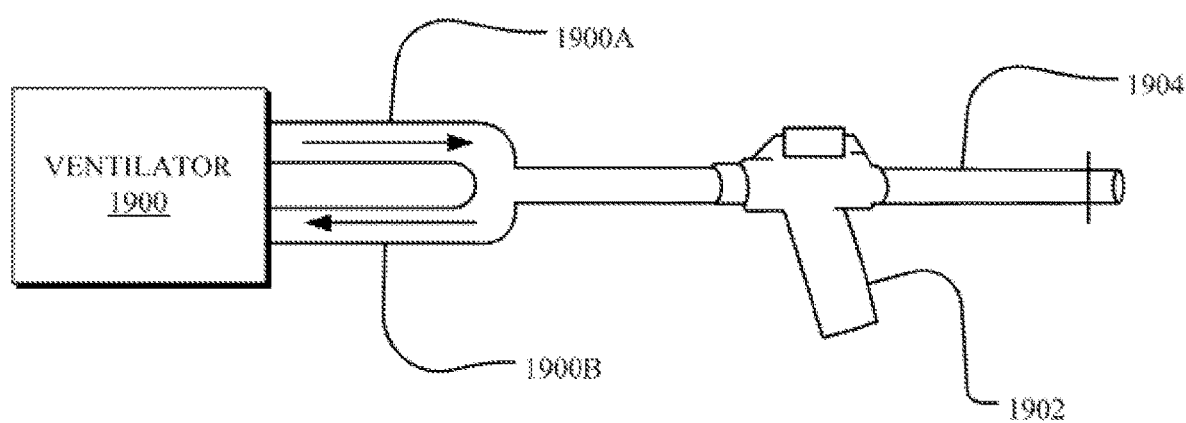
FIG. 6 illustrates a system comprising a droplet delivery device in combination with a mechanical ventilator, in accordance with certain embodiments of the disclosure.

As such, with reference to FIG. 6, an embodiment of the disclosure is provided wherein a dry powder delivery device 1902 is placed in-line with a ventilator 1900, (for example a GE Carescape R860). The dry powder delivery device 1902 generates a plume of particles as described herein, which includes a therapeutic agent such as tobramycin, that enters into the ventilator airplume near to the patient end of the endotracheal tube 1904. FIG. 19 provides an example of a standalone device 1902 operating with a ventilator 1900. The ventilator 1900 supplies a plume of inhalation air 1900A and removes a plume of exhalation air 1900B in separate tubes that merge to a single endotracheal tube 1904 close to the patient to minimize mixing of inhalations and exhalations and dead volume. The dry powder delivery device 1902 may be placed close to the patient end of the endotracheal tube 1904 in order to minimize loss of particles that may stick to the tube sidewall. The patient end of the endotracheal tube 1904 is placed in a patient's throat and held in place with a balloon near the end of the tube (not shown).

Actuation of the dry powder delivery device is initiated at the start of an inhalation cycle. The dry powder delivery device can be battery powered and self-initiating breath actuated or connected to electronics that are part of the ventilator. The system may be configured so that dosing frequency and duration may be set either within the ventilator or the device. Similarly, plume generation timing and duration can be determined by the device or initiated by the ventilator. For example, the device may be programmed to dispense for half a second once every ten breaths on a continuous basis or perhaps once a minute. A dry powder delivery device may operate in a standalone manner or communicate the timing of dispenses and flowrates to the ventilator by a direct electrical connection or via Bluetooth or a similar wireless protocol.

Another aspect of the disclosure provides a system which may also be used with conventional portable CPAP machines to deliver therapeutic agents, e.g., where continuous or periodic dosing during the course of the night is valuable. In another embodiment, the dry powder delivery devices of the disclosure many be used in connection with a portable CPAP machine to prevent and treat cardiac events during sleep.

Typically CPAP machines use a mask to supply positive air pressure to a patient while sleeping. Applications of the dry powder delivery devices in conjunction with CPAP machines may provide an efficient method for continuous dosing of therapeutic agents such as antibiotics, cardiac medications, etc., for outpatient treatment of diseases, conditions, or disorders, such as pneumonia, atrial fibrillation, myocardial infarction, or any disease, condition, or disorder where continuous or periodic nighttime delivery of a medicine is desired.

In sleep apnea (SA) there are periods of not breathing and an associated decline in blood oxygen level. Not surprisingly, cardiac failure or "heart attacks" are associated with sleep apnea. This association is thought to be due to both the stress on the heart related to low oxygen levels and the increased stress on the heart as the body requires increased blood pressure and cardiac output from the heart. Additionally, there is increased risk of sleep apnea in older and overweight adults. Thus those with SA have a higher risk of heart attacks than the general population because the SA stresses the heart and because the risk factors associated with SA are very similar to the risk factors for heart attacks.

The Journal of New England in 2016 published a four-year study of the effects of CPAP on 2700 men with sleep apnea and found that CPAP significantly reduced snoring and daytime sleepiness and improved health-related quality of life and mood. (R. Doug McEvoy, et al. CPAP for Prevention of Cardiovascular Events in Obstructive Sleep Apnea, *N. ENGL. J. MED.* 375; 10 nejm.org Sep. 8, 2016). However, the use of CPAP did not significantly reduce the number of cardiac events. The article noted that "Obstructive sleep apnea is a common condition among patients with cardiovascular disease, affecting 40 to 60% of such patients."

Many of these cardiac events can be lessened by administration of the proper medication. For example, beta blockers such as Metoprolol can lessen atrial fibrillation and the effects of myocardial infarction to sufficient extent as to prevent death in such an episode.

In certain aspects of the disclosure, the need to lessen adverse cardiac events in the population of people using CPAP devices by sensing the presence of the event and administering an ameliorating drug via pulmonary delivery is addressed. Specifically, a cardiac event may be detected by conventionally available means to detect and evaluate cardiac condition. These include heart rate monitors (such as electrical sensors held in place by an elastic band across the chest or optical monitoring at the earlobe, finger or wrist), automated blood pressure cuffs, or blood-oxygen saturation monitors on the finger or ear). When the monitor detects an adverse condition a specific dose of appropriate drug is administered by a particle delivery device of the disclosure via the CPAP tube or mask so that the drug is inhaled and carried to the blood plume via deep inhalation into the lung. Pulmonary administration is optimized both by the generation of particles less than 5 microns in size and delivery of the particles at the beginning of an inhalation cycle.

Figure 7:
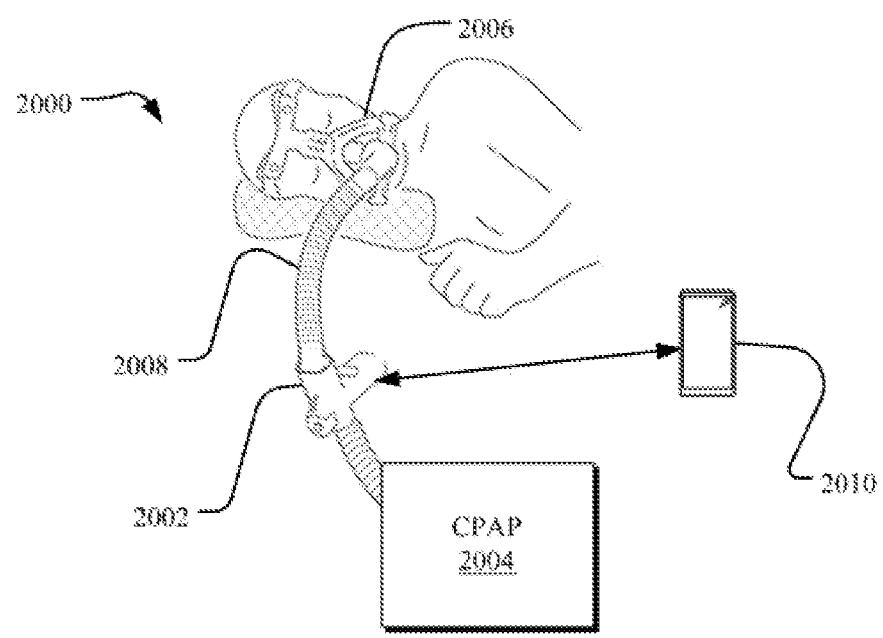
FIG. 7 illustrates a system comprising a droplet delivery device in combination with a CPAP machine, e.g., to assist with cardiac events during sleep, in accordance with certain embodiments of the disclosure.

Referring to FIG. 7, a schematic representation and example for the use of a system 2000 including dry powder delivery device 2002 of the disclosure with a CPAP machine 2004 to assist with cardiac events during sleeping. In certain aspects of the disclosure described herein, the patient is shown sleeping with a CPAP mask 2006 in place and pressurized air is delivered to the mask 2006 by the CPAP machine 2004. Cardiac condition is monitored by optical measurement of the heartbeat either at finger, toe, ear lobe or the wrist (not shown). The dry powder delivery device 2002 may be placed in-line with the tube 2008 between the CPAP machine 2004 and the CPAP mask 2006, or alternative may be placed at the airflow entrance of CPAP mask 2006 (not shown). Breathing is monitored by airflow measurement in the tube 2008 from the CPAP machine 2004 to the CPAP mask 2006. Airflow rate and direction can be measured by measuring the pressure on either side of a screen which adds a slight amount of airflow restriction. Typically there will be continuous positive airflow which increases in flow rate at inspiration. A controller detects abnormal cardiac condition such as an increase in atrial fibrillation and triggers generation of particles of an anti-arrhythmic drug at the start of an inhalation cycle as detected by airflow in the CPAP supply tube. Information may be recorded and stored in a patient's smartphone 2010, and various alerts may be sounded if a cardiac event is detected (e.g., transmitted via Bluetooth or other wireless communication methodology), if desired. Further, the patient's condition and drug dispenses may be monitored via a smartphone app, providing the patient and his medical provider with an accurate record of the patient's condition.

Other diseases commonly associated with sleep apnea, use of a mechanical ventilator, or a CPAP machine may also benefit from a system which non-invasively monitors patient condition and provides pulmonary administration of the appropriate ameliorating medication via a particle delivery device of the disclosure. For example, those with diabetes frequently are concerned that low blood sugar from a slight insulin overdose will lead to unconsciousness. In this case, abnormally low heartrate, breathing or blood pressure can be detected and sugar or insulin administered via particles to the pulmonary system.

All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed:

1. A breath actuated dry powder delivery device for delivering a dry powder as a plume of particles to a pulmonary system of a subject, the device comprising:
    a housing comprising a mouthpiece located at an airflow exit side of the housing, and a laminar flow element;
    a cartridge disposed within or removably attached to the housing, for receiving a volume of powder;
    a powder dispersion mechanism, the powder dispersion mechanism comprising an energy source configured to generate and disperse a plume of particles from the volume of powder received in the cartridge;
    at least one differential pressure sensor positioned between the powder dispersion mechanism and the airflow exit side within the housing;
    the at least one differential pressure sensor configured to activate the energy source of the powder dispersion mechanism upon sensing a pre-determined pressure change within the housing to thereby generate the plume of particles;
    the laminar flow element located at an airflow entrance side of the housing, wherein the housing, the laminar flow element, and the mouthpiece are configured to facilitate laminar airflow across an exit side of the powder dispersion mechanism and to provide sufficient laminar airflow through the housing during use;
    the dry powder delivery device configured such that the plume of particles are directed into and through the housing at an approximate 90 degree change of trajectory prior to expulsion from the housing;
    the powder dispersion mechanism configured to generate the plume of particles wherein at least about 70% of the particles in the plume of particles have an average particle diameter of less than about 6 microns; and
    wherein the energy source comprises a compressed gas source.

2. The dry powder delivery device of claim 1, wherein the compressed gas source is a $CO_2$ compressed gas source.

3. The dry powder delivery device of claim 1, wherein the cartridge is configured as a rotatable disk comprising one or more unit dose reservoirs configured for receiving a unit dose of powder.

4. The dry powder delivery device of claim 1, further comprising a wireless communication module.

5. The dry powder delivery device of claim 1, wherein the device further comprises one or more sensors selected from an infrared transmitter, a photodetector, an additional pressure sensor, and combinations thereof.

6. A method for generating and delivering a powder as a plume of particles to a pulmonary system of a subject in a respirable range, the method comprising:
    (a) generating a plume of particles via the breath actuated dry powder delivery device of claim 1, wherein at least 70% of the particles in the plume of particles have an average particle diameter of less than about 6 microns; and
    (b) delivering the plume of particles to a pulmonary system of a subject such that at least 70% of a mass of the generated particles is delivered in a respirable range to the pulmonary system of the subject during use.

7. The method of claim 6, wherein the plume of particles is delivered for a treatment of a pulmonary disease, disorder or condition.

8. The method of claim 7, wherein the pulmonary disease, the disorder, or the condition is asthma, chronic obstructive pulmonary diseases (COPD), cystic fibrosis (CF), tuberculosis, chronic bronchitis, or pneumonia.

9. The method of claim 6, wherein the particles comprise a COPD medication, an asthma medication, an antibiotic, or a combination thereof.

* * * * *